US010517964B2

(12) United States Patent
Gambhir et al.

(10) Patent No.: US 10,517,964 B2
(45) Date of Patent: Dec. 31, 2019

(54) OPTICAL IMAGING PROBES, OPTICAL IMAGING SYSTEMS, METHODS OF OPTICAL IMAGING, AND METHODS OF USING OPTICAL IMAGING PROBES

(75) Inventors: Sanjiv S. Gambhir, Portola Valley, CA (US); Zhen Cheng, Mountain View, CA (US); Sri-rajasekhar Kothapalli, Mountain View, CA (US); Hongguang Liu, Palo Alto, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 1452 days.

(21) Appl. No.: 13/406,891

(22) Filed: Feb. 28, 2012

(65) Prior Publication Data

US 2012/0220870 A1 Aug. 30, 2012

Related U.S. Application Data

(60) Provisional application No. 61/448,285, filed on Mar. 2, 2011, provisional application No. 61/447,445, filed on Feb. 28, 2011.

(51) Int. Cl.
| A61K 49/00 | (2006.01) |
| A61K 51/00 | (2006.01) |
| A61K 51/04 | (2006.01) |
| B82Y 30/00 | (2011.01) |
| A61B 6/00 | (2006.01) |
| A61B 5/00 | (2006.01) |
| A61B 6/03 | (2006.01) |

(52) U.S. Cl.
CPC .......... *A61K 49/0013* (2013.01); *A61B 6/508* (2013.01); *A61K 51/00* (2013.01); *A61K 51/0491* (2013.01); *B82Y 30/00* (2013.01); *A61B 5/0075* (2013.01); *A61B 6/037* (2013.01)

(58) Field of Classification Search
CPC ............ A61K 49/0013; A61K 51/0491; A61K 51/00; A61B 6/508; A61B 6/037; A61B 5/0075; B82Y 30/00
USPC .......................... 600/407, 431, 436, 473–478
See application file for complete search history.

(56) References Cited

U.S. PATENT DOCUMENTS

| 6,937,696 | B1 | 8/2005 | Mostafavi | |
| 7,394,053 | B2 * | 7/2008 | Frangioni et al. | ......... 250/208.1 |
| 8,229,548 | B2 | 7/2012 | Frangioni | |
| 2006/0261325 | A1 * | 11/2006 | Zanrosso et al. | ............... 257/14 |
| 2007/0238957 | A1 * | 10/2007 | Yared | ................... A61B 5/0059 600/407 |
| 2011/0098353 | A1 | 4/2011 | Dilworth et al. | |

\* cited by examiner

*Primary Examiner* — Peter Luong
(74) *Attorney, Agent, or Firm* — Thomas|Horstemeyer, LLP

(57) ABSTRACT

Embodiments of the present disclosure provide for radionuclide probes, methods of using the radionuclide probes, methods of detecting an optical signal from radionuclides, methods of detecting an optical signal from a quantum dot(s) that receives optical energy from a radionuclide(s), system for analyzing optical energy emitted by a radionuclide(s), system for imaging a target within a living subject or a sample, methods of imaging a disease or condition, and the like.

23 Claims, 18 Drawing Sheets
(16 of 18 Drawing Sheet(s) Filed in Color)

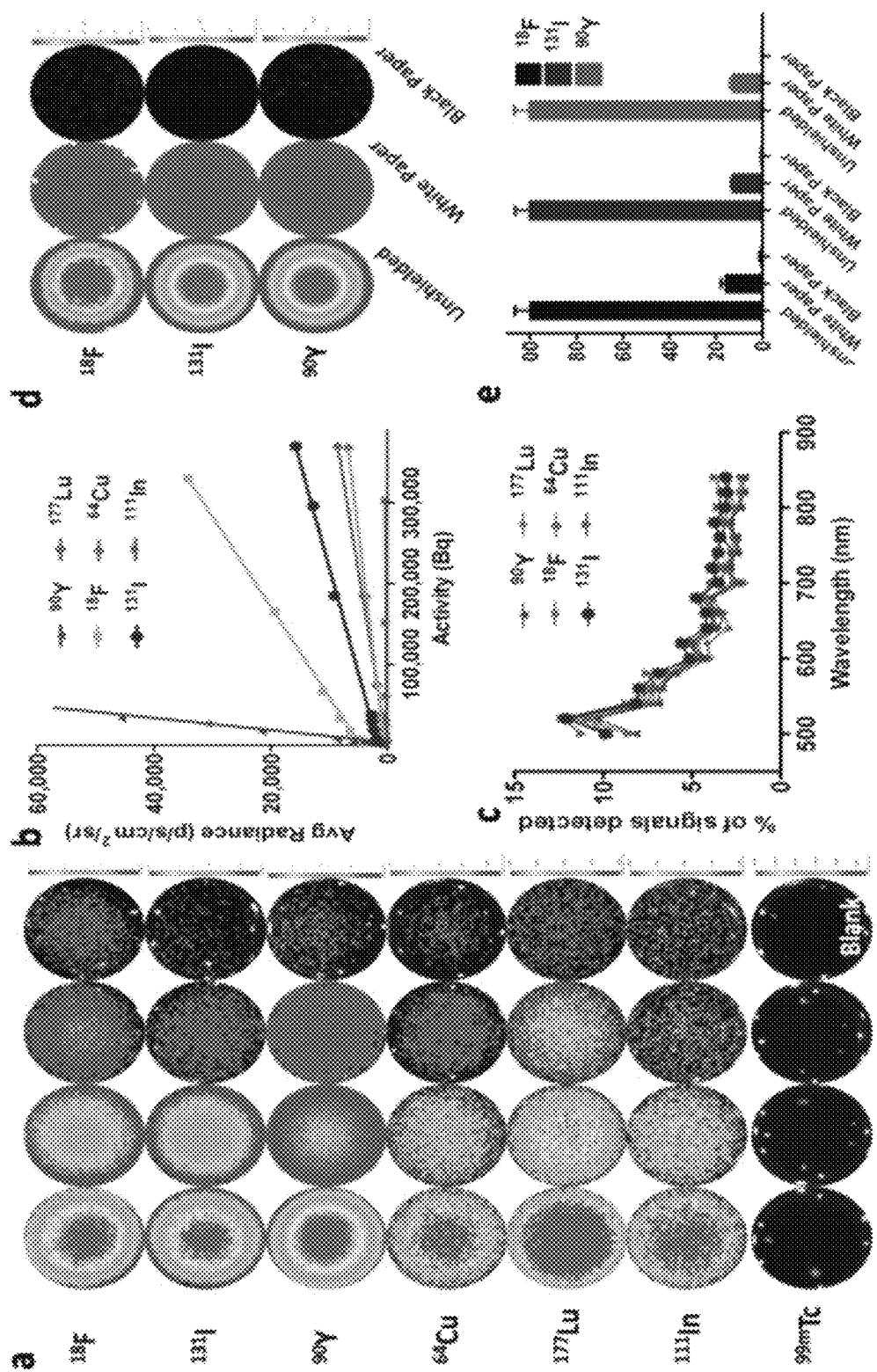
FIG. 1.1

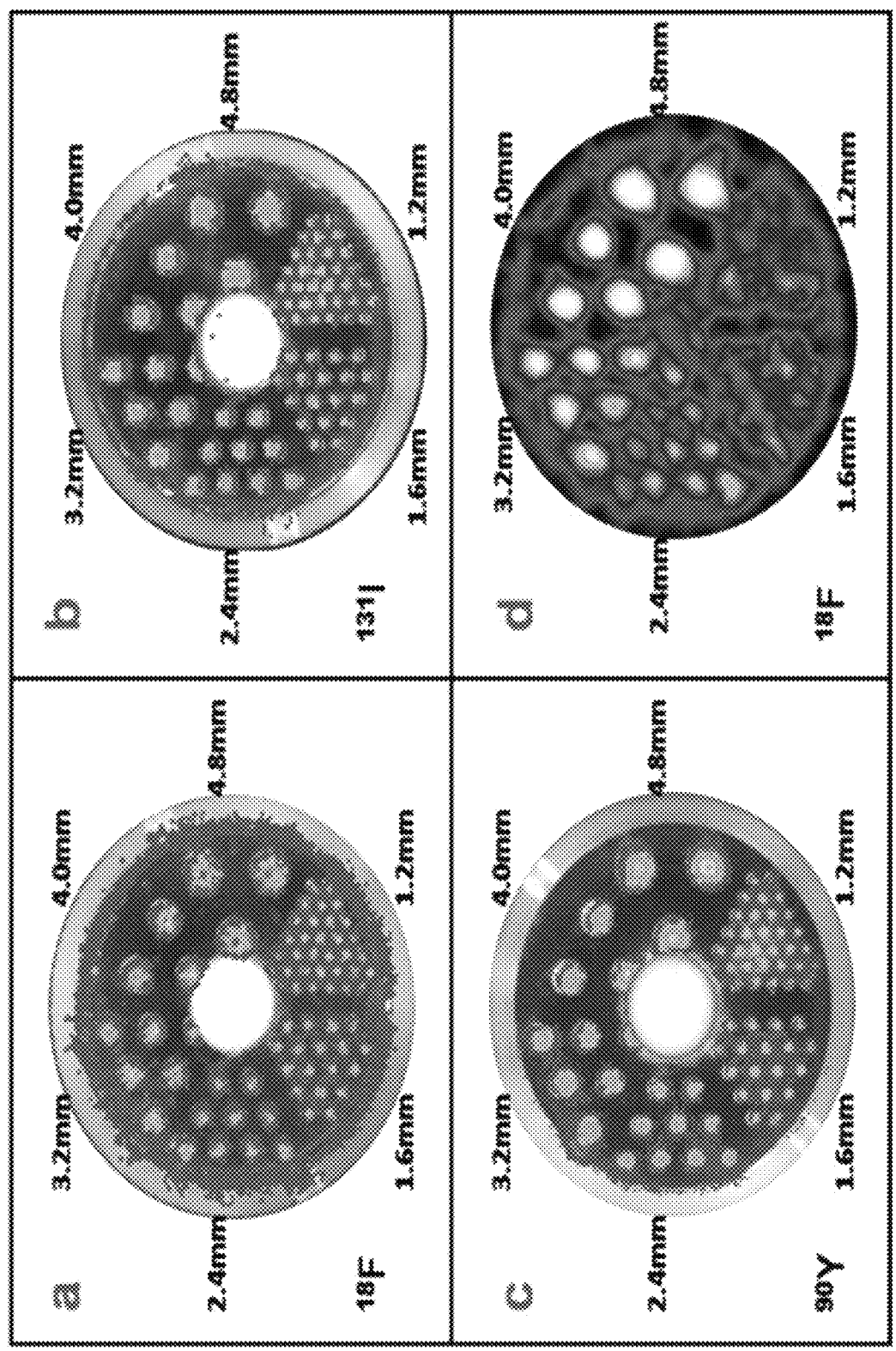
FIG. 1.2

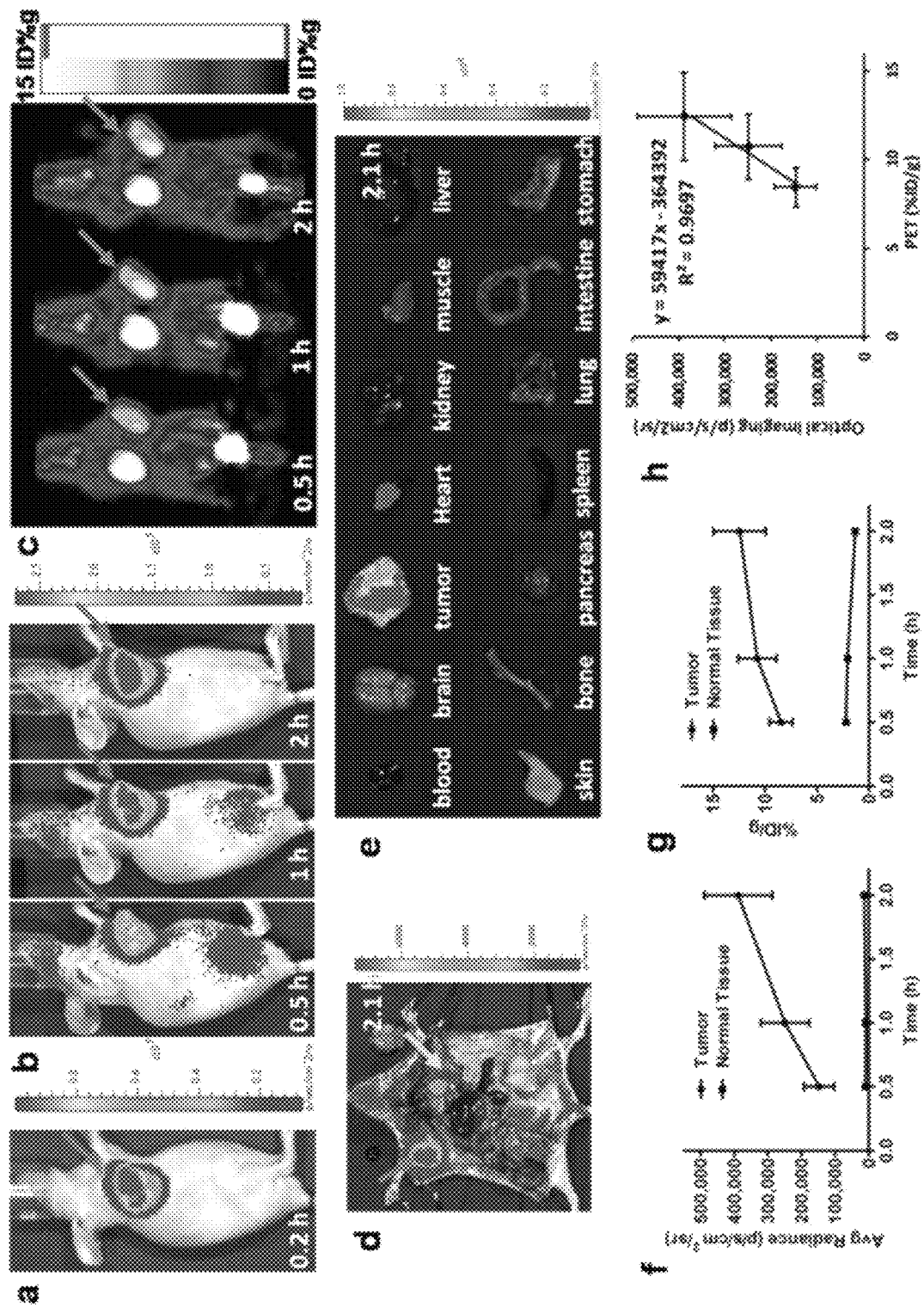
FIG. 1.3

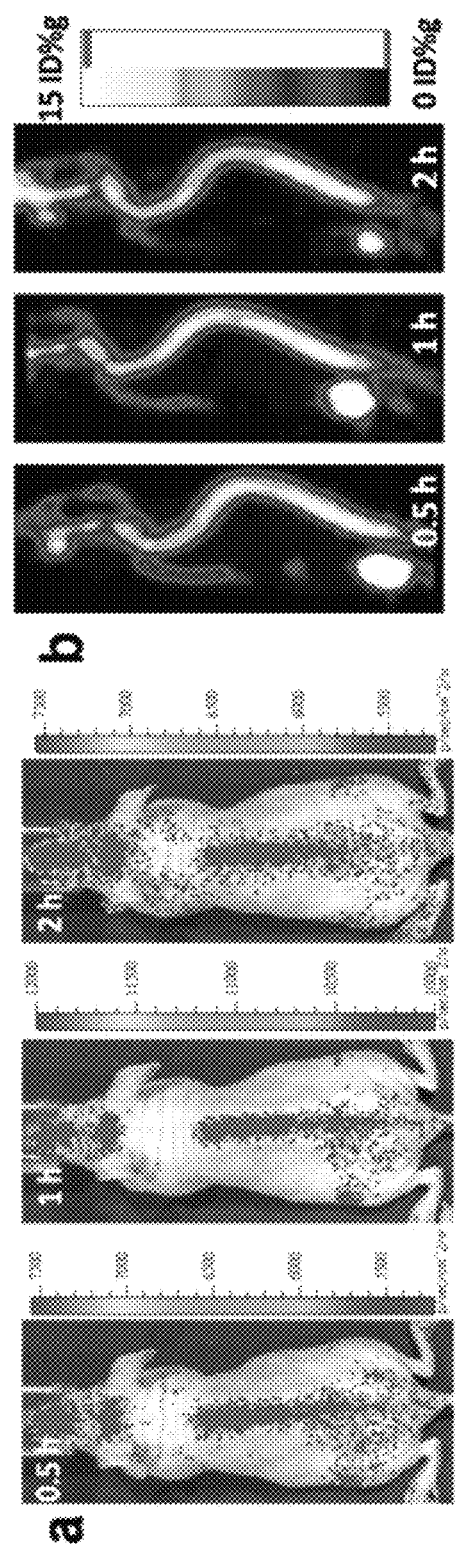
FIG. 1.4

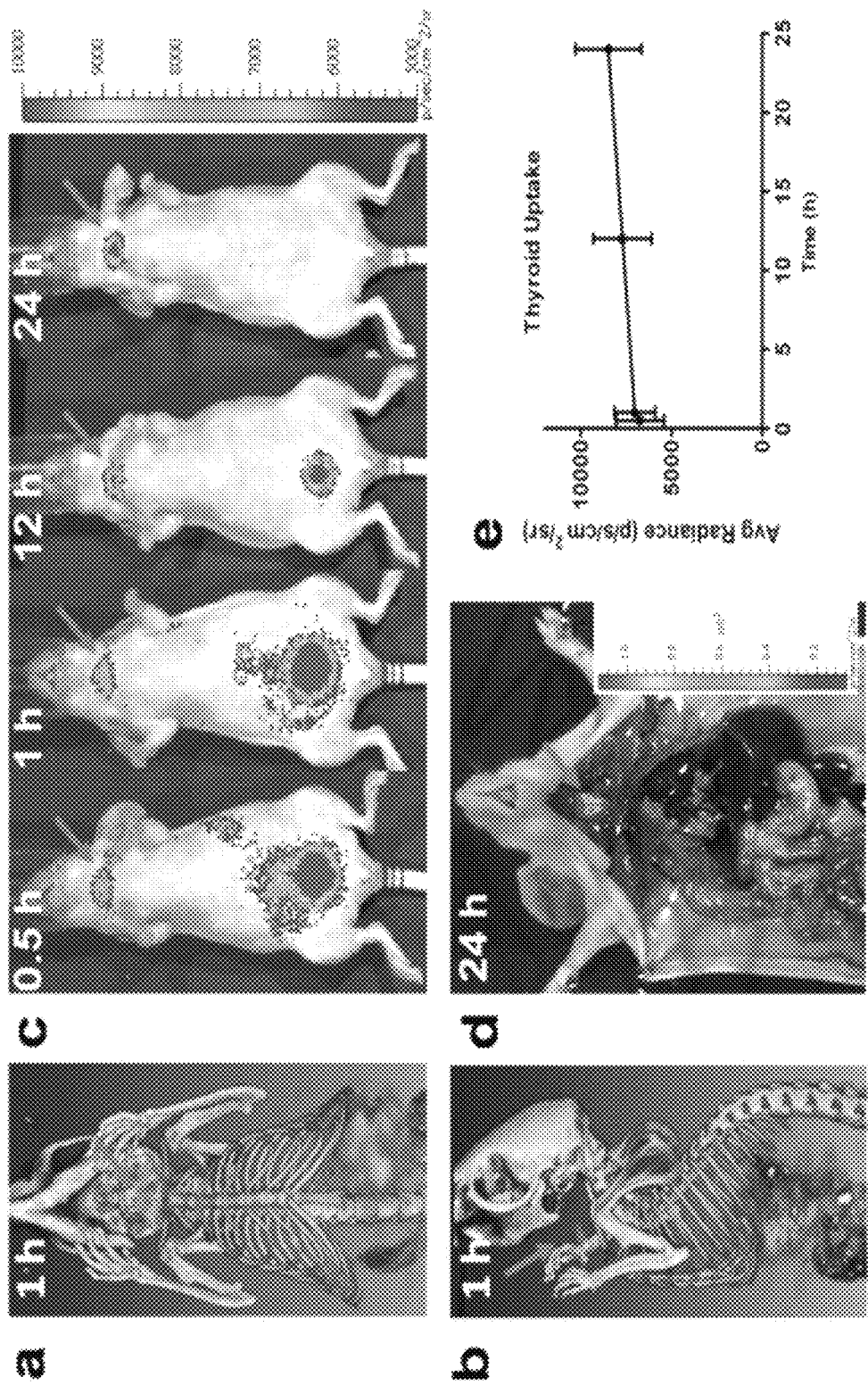
FIG. 1.5

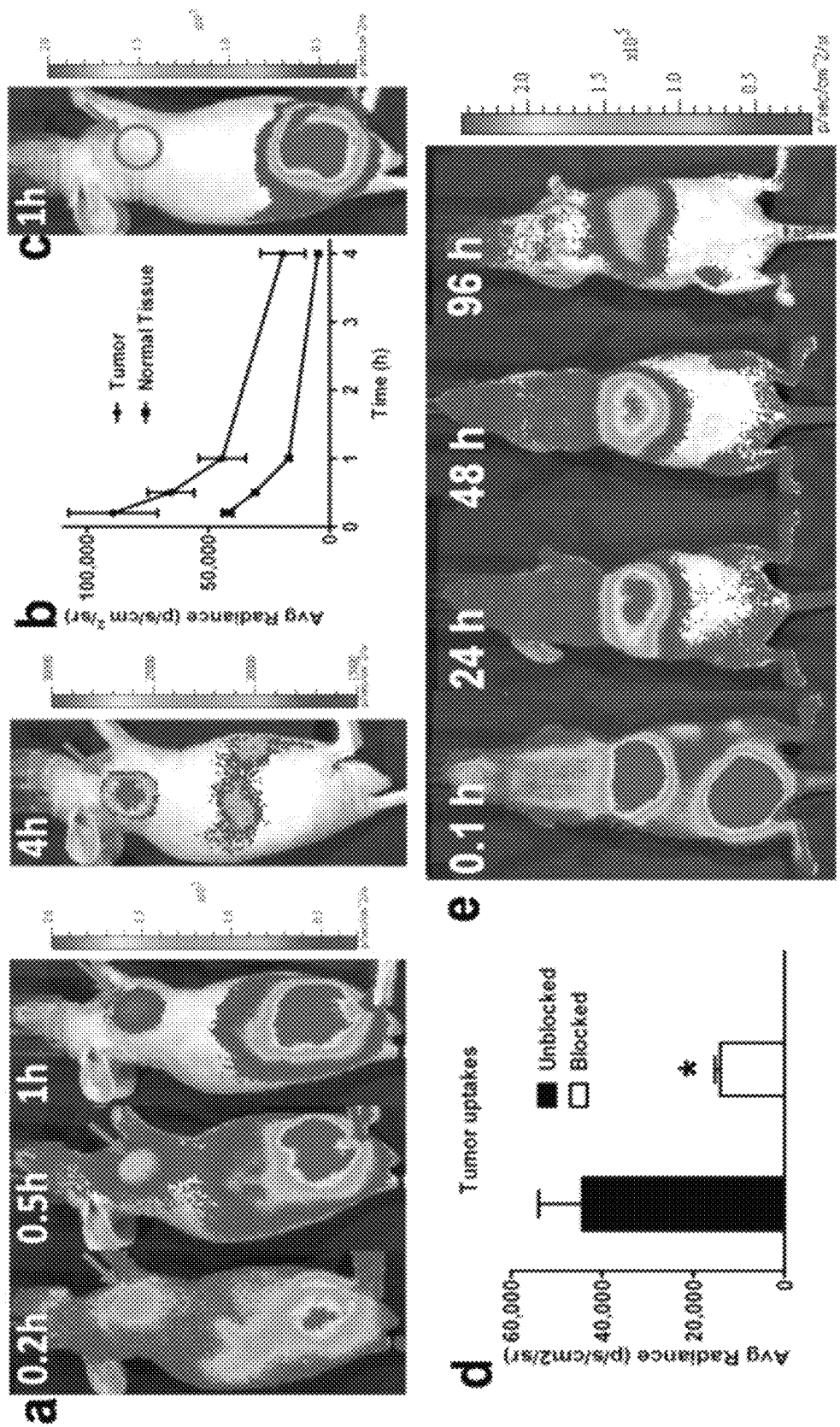
FIG. 1.6

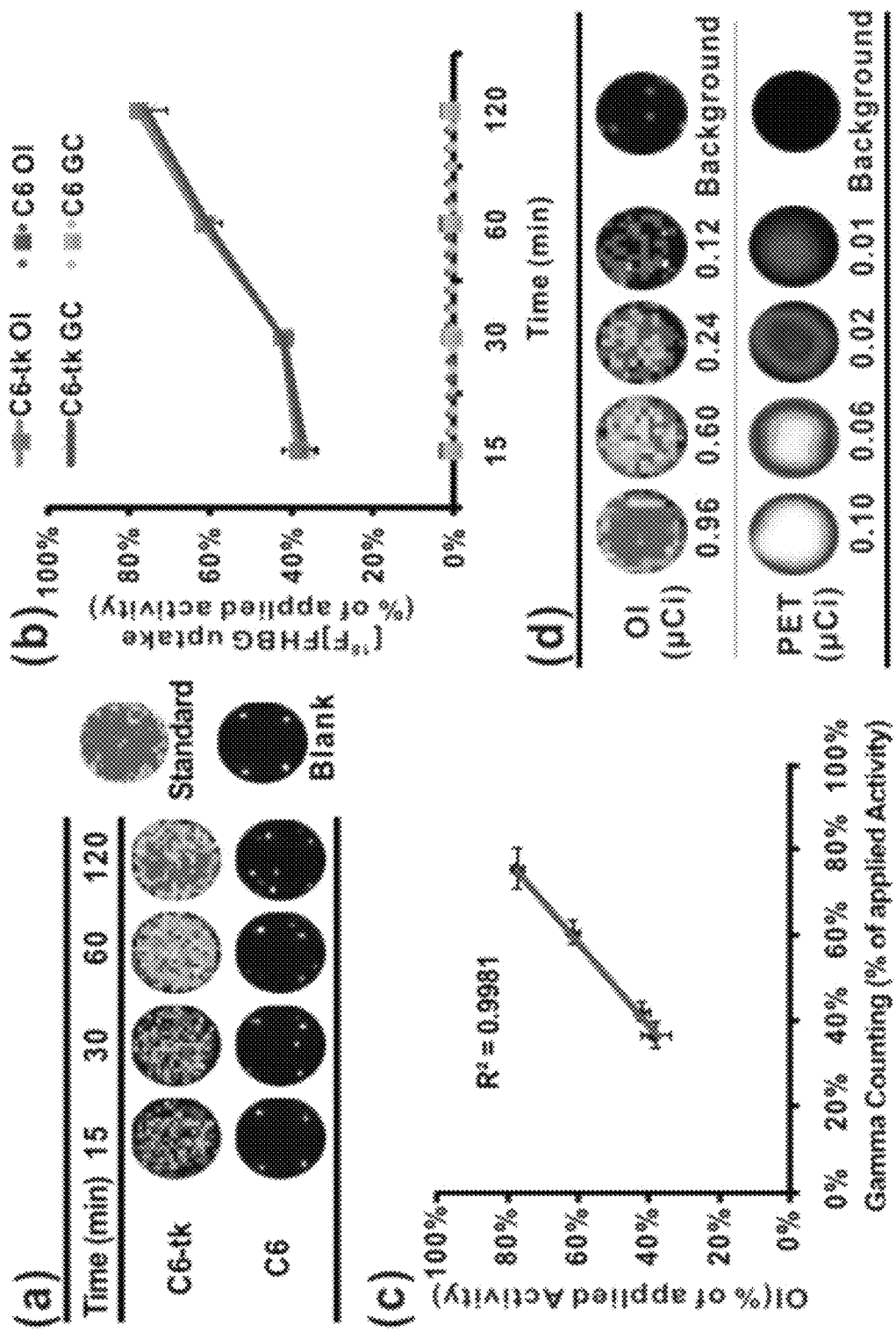
FIG. 2.1

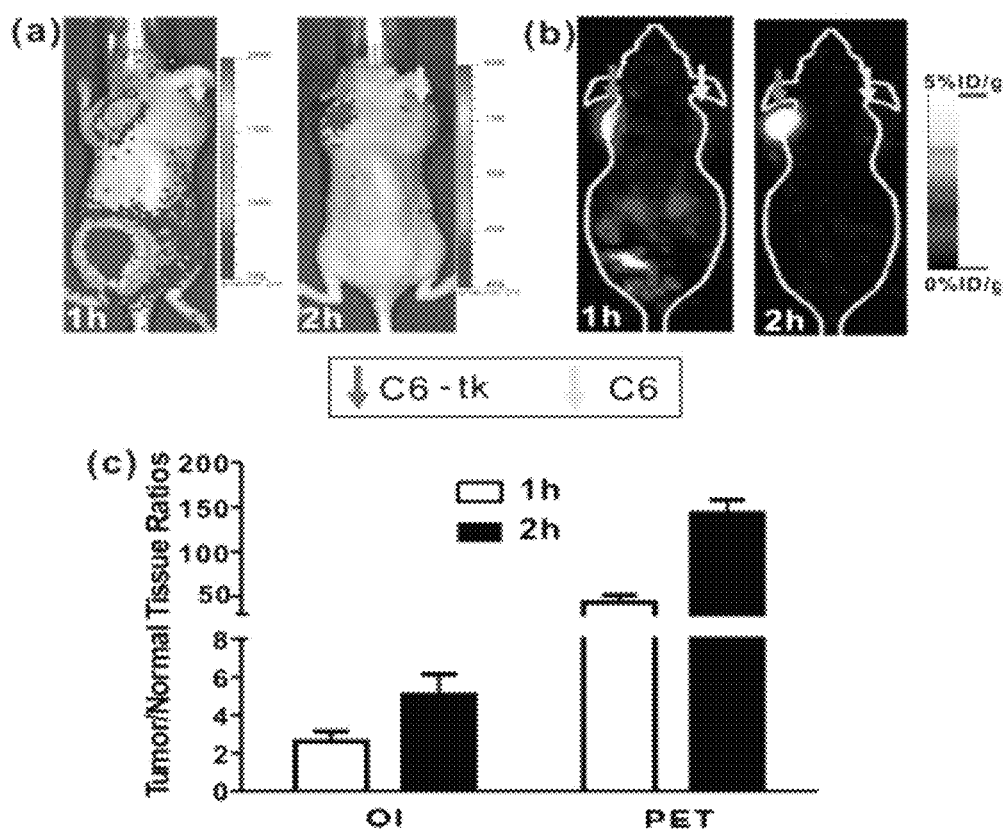
FIG. 2.2

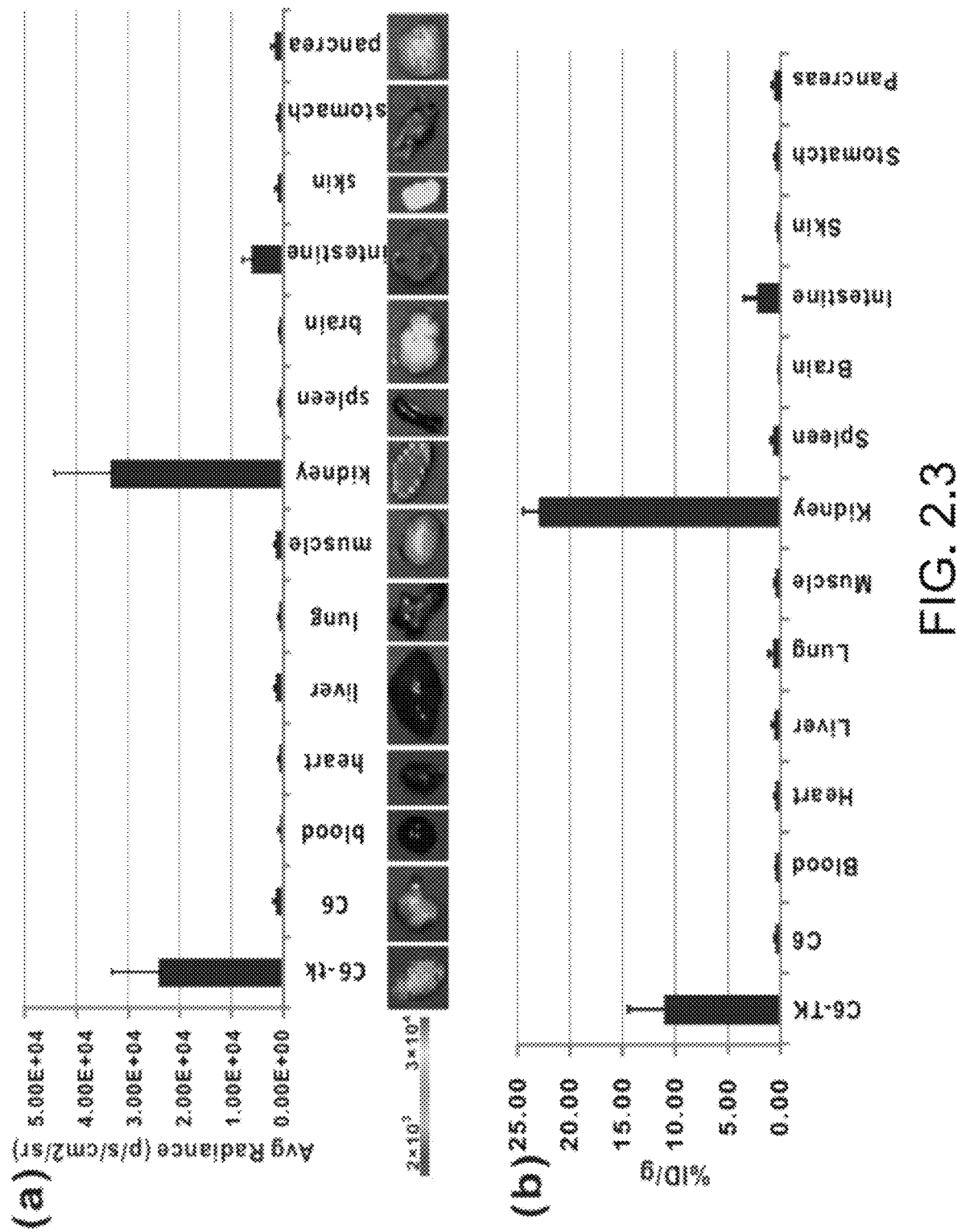
FIG. 2.3

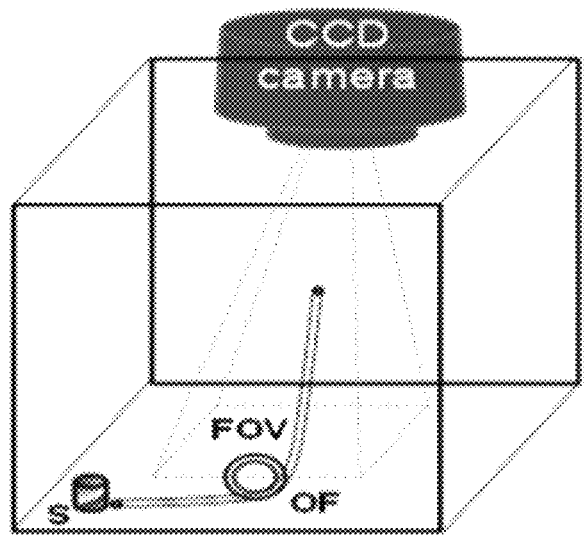
FIG. 3.1
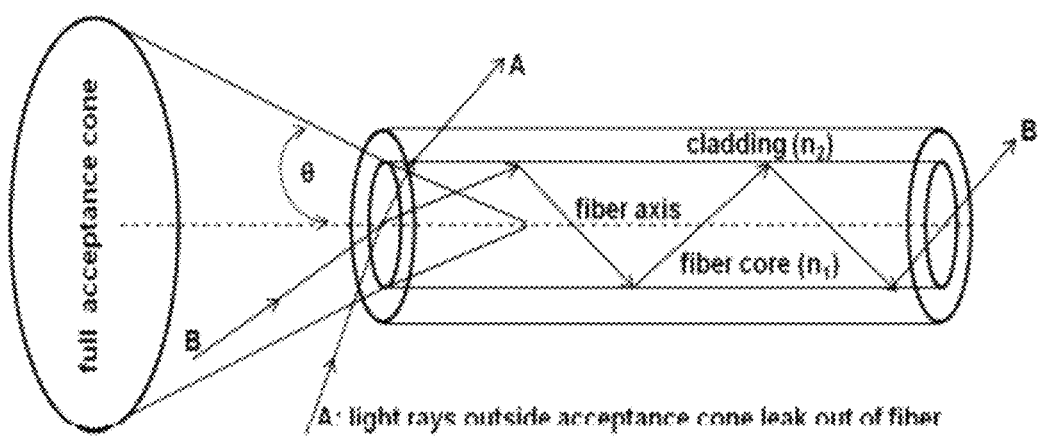
FIG. 3.2

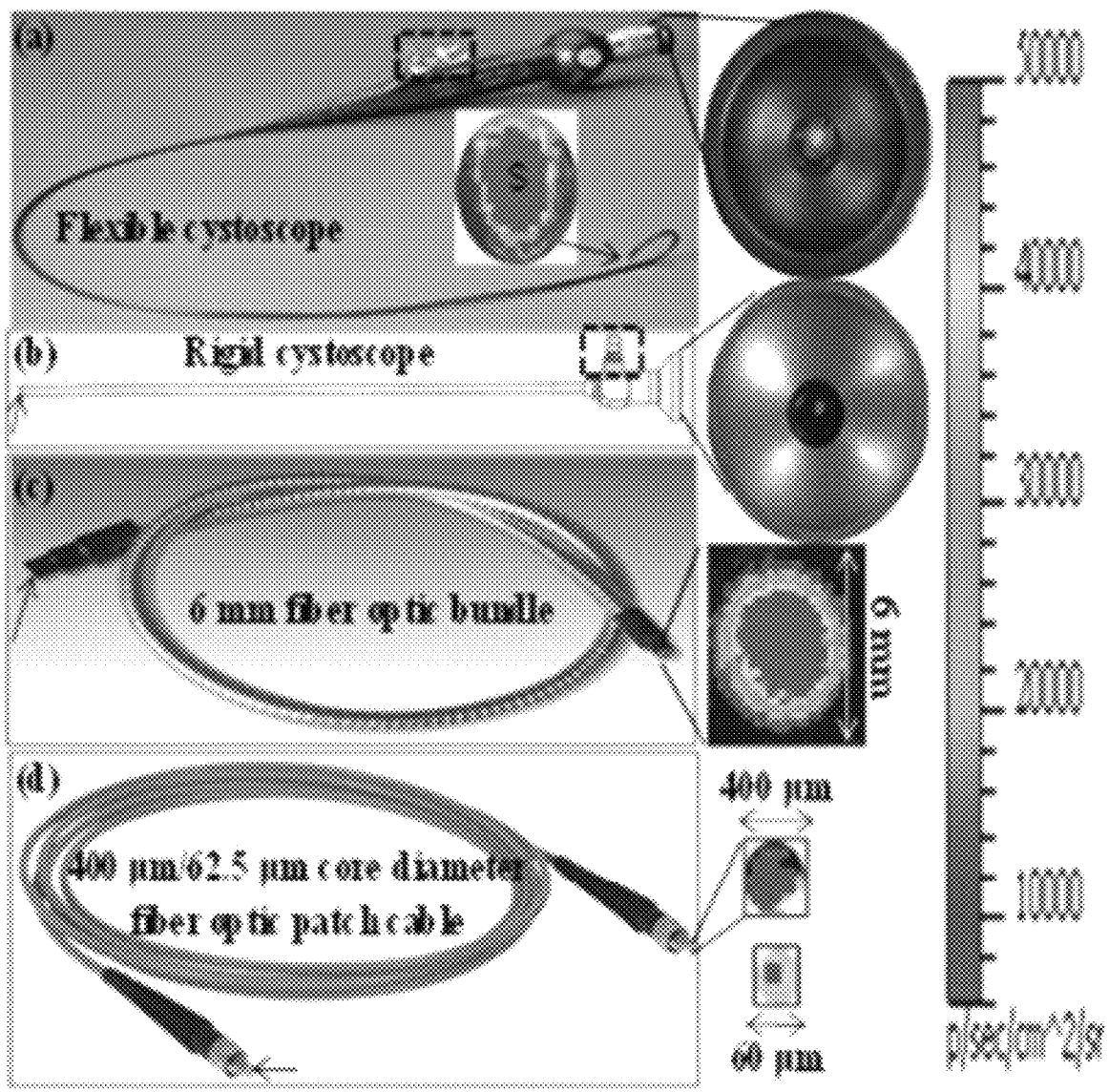
FIG. 3.3

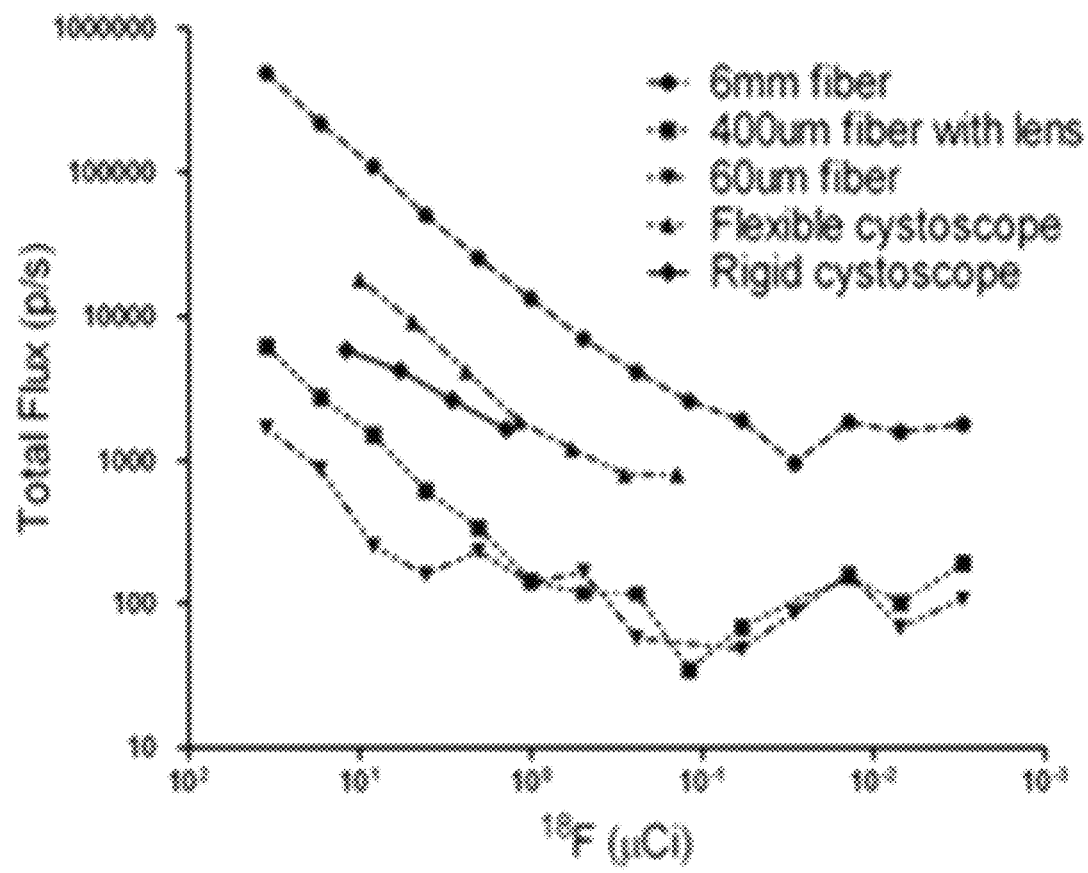
FIG. 3.4

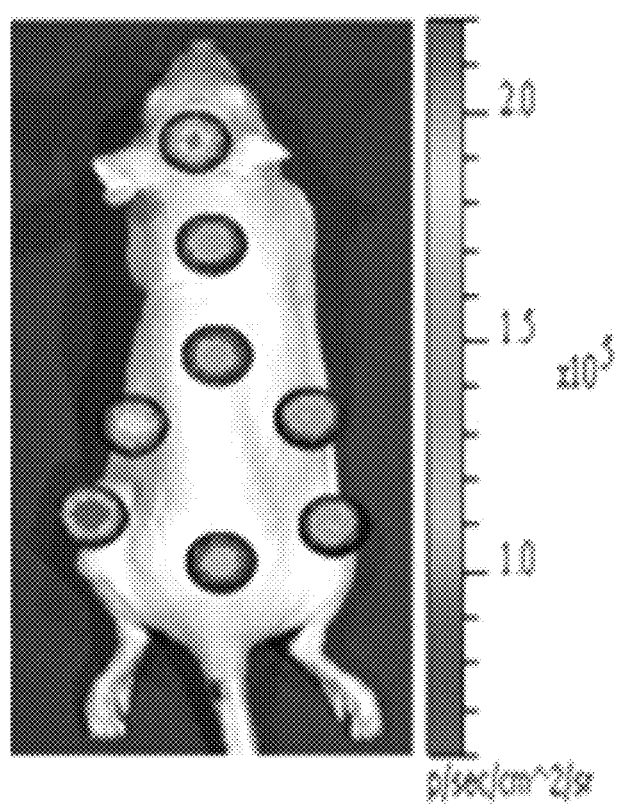
FIG. 3.5

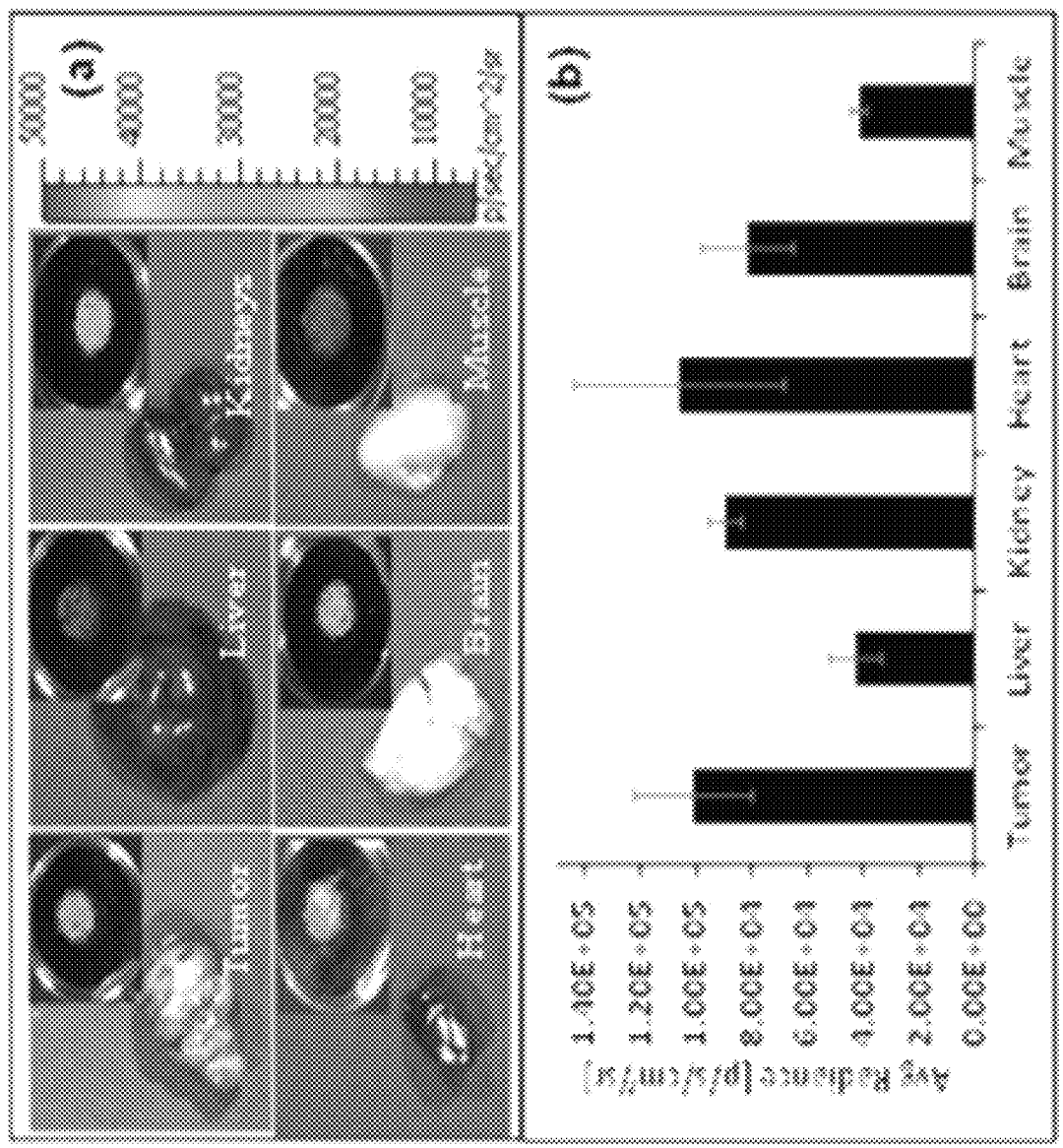
FIG. 3.6

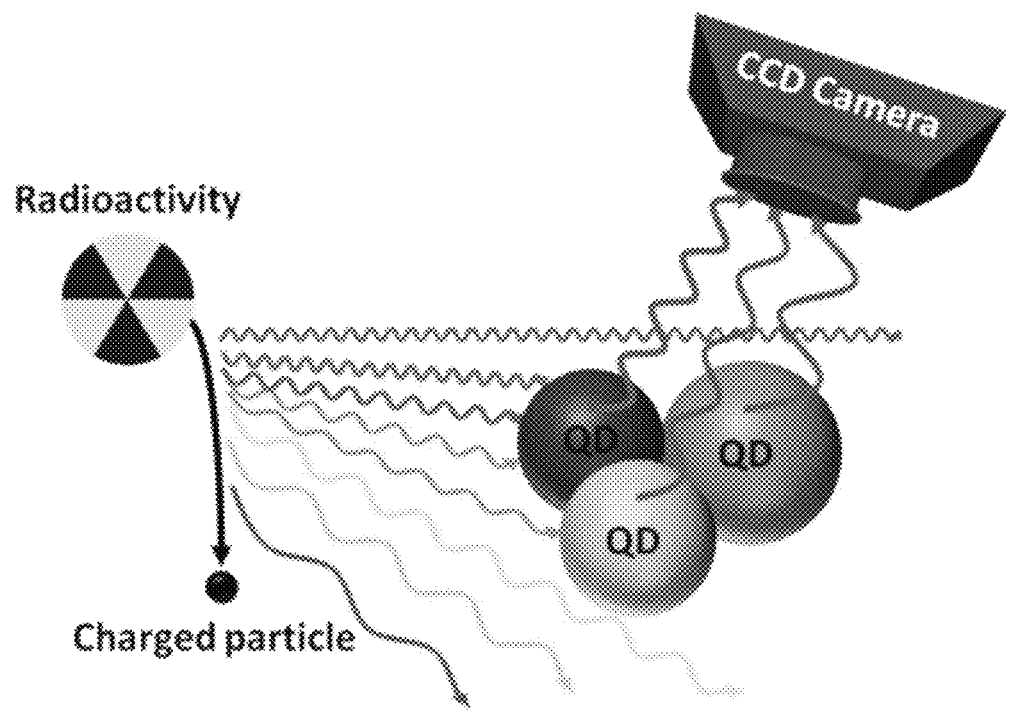
FIG. 4.1

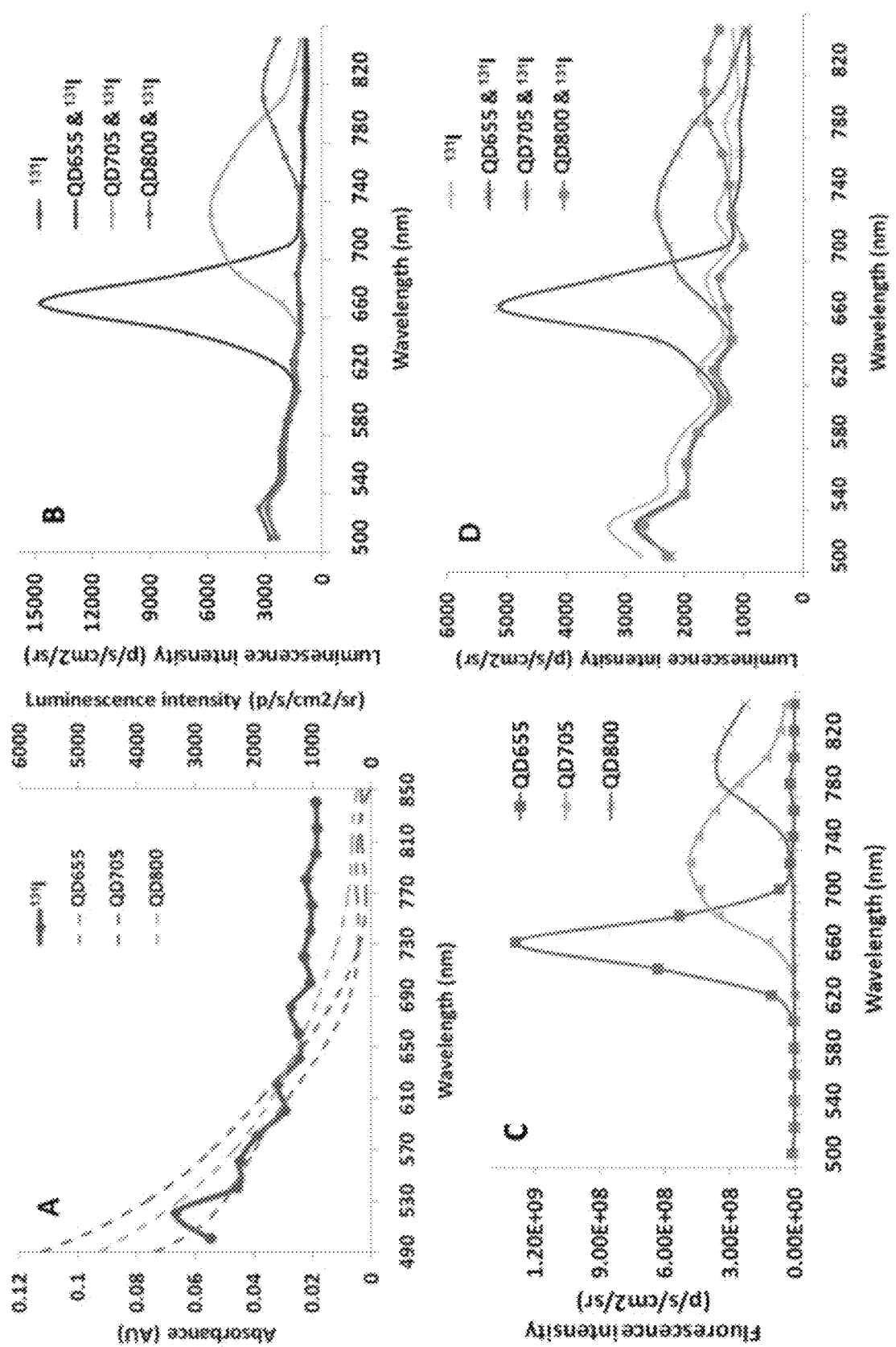
FIG. 4.2

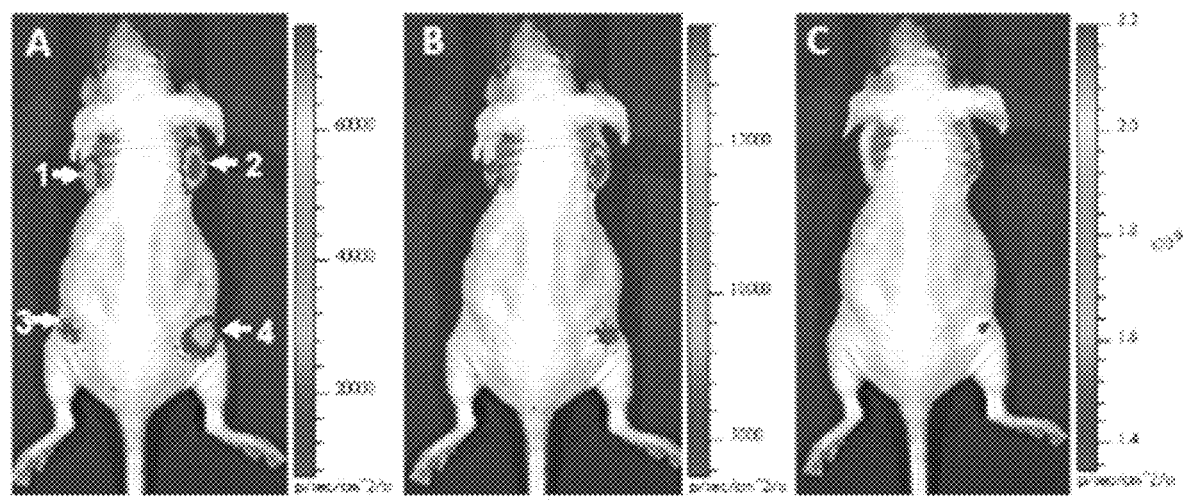
FIG. 4.3
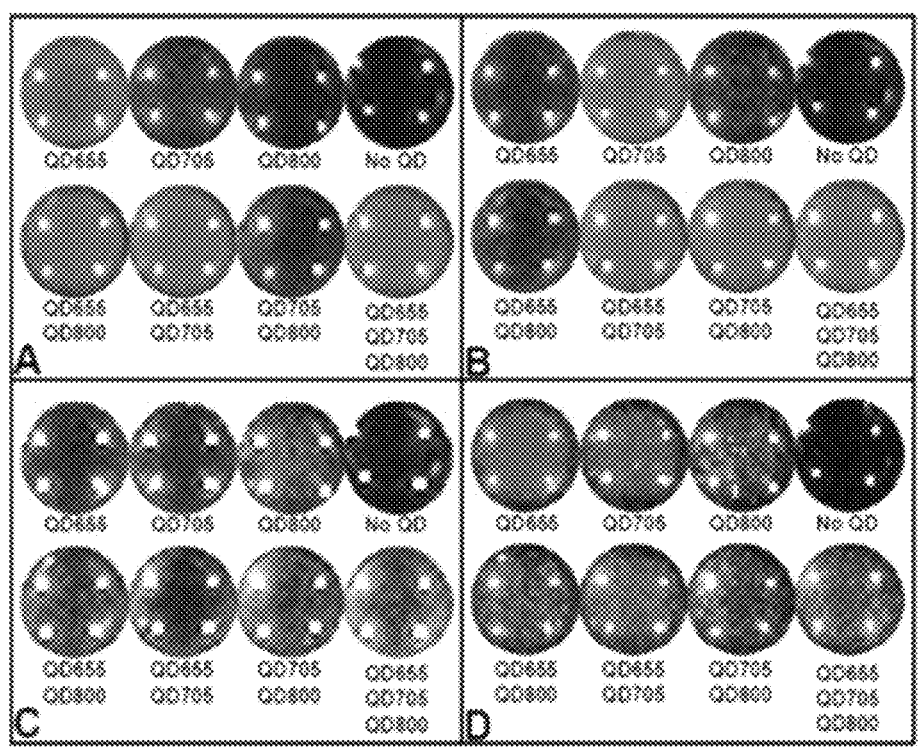
FIG. 4.4

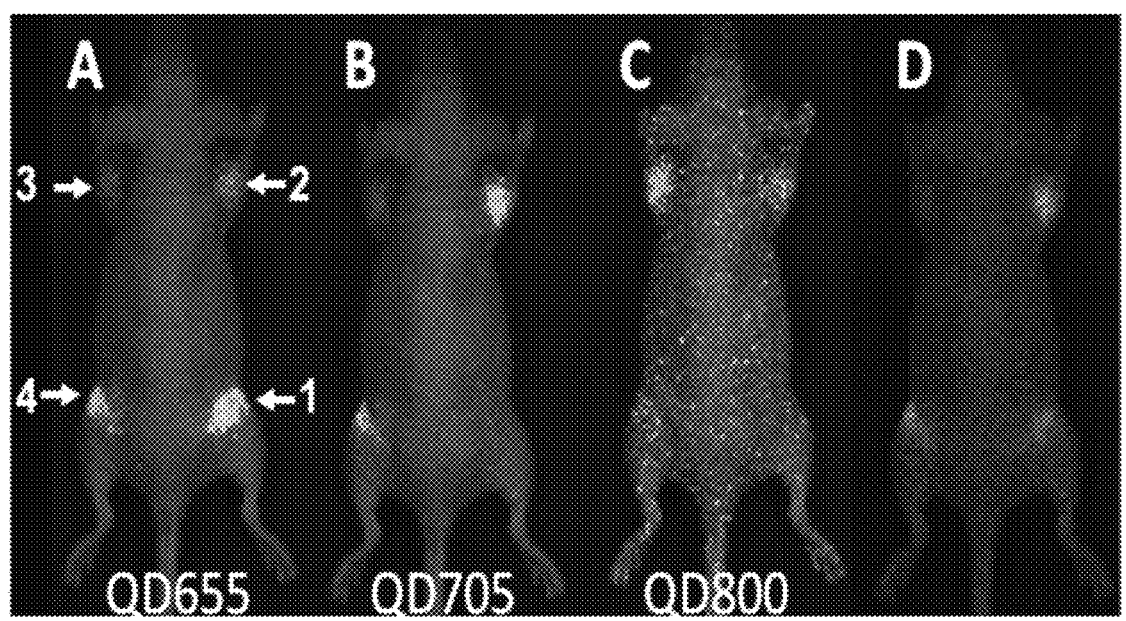
FIG. 4.5

OPTICAL IMAGING PROBES, OPTICAL IMAGING SYSTEMS, METHODS OF OPTICAL IMAGING, AND METHODS OF USING OPTICAL IMAGING PROBES

CROSS-REFERENCE TO RELATED APPLICATION

This application claims priority to U.S. provisional application entitled "Optical Molecular Imaging Methods and Systems," having Ser. No. 61/447,445, filed on Feb. 28, 2011, which is entirely incorporated herein by reference. In addition, this application claims priority to U.S. provisional application entitled "Optical Molecular Imaging Methods and Systems," having Ser. No. 61/488,285, filed on May 20, 2011, which is entirely incorporated herein by reference.

FEDERAL SPONSORSHIP

This invention was made with Government support under Contract/Grant Nos. NIH CA121842, NIH CA119367, and NIH CA114747, awarded by the National Institute of Health (NIH). The Government has certain rights in this invention.

BACKGROUND

Molecular imaging is a relatively new and fast growing research discipline, which has the ability to study diseases non-invasively in living subjects at the molecular level. Numerous researches have demonstrated that molecular imaging techniques play a central role in the era of personalized medicine. A variety of imaging modalities have been developed for providing functional and anatomical information of diseases in living small animals and patients, which include positron emission tomography (PET), single photon emission computed tomography (SPECT), optical imaging (OI, bioluminescence and fluorescence), magnetic resonance imaging (MRI), ultrasound (US), and computed tomography (CT).

Radioactive molecular probes are traditionally imaged with PET, SPECT or gamma (γ) cameras, by taking advantages of the capability of these imaging modalities to detect the high energetic γ rays. Whereas OI generally detects low energy lights (visible or near-infrared lights) emitted from bioluminescence or fluorescence probes. So far there has not been any overlap between radioactive probes and conventional OI techniques.

SUMMARY

Embodiments of the present disclosure provide for radionuclide probes, methods of using the radionuclide probes, methods of detecting an optical signal from radionuclides, methods of detecting an optical signal from a quantum dot(s) that receives optical energy from a radionuclide(s), systems for analyzing optical energy emitted by a radionuclide(s), systems for imaging a target within a living subject or a sample, methods of imaging a disease or condition, and the like.

An embodiment of the method of imaging a target within a living subject or a sample, among others, includes: introducing one or more radionuclide probes into the living subject or sample; and detecting low energy photons generated by the one or more radionuclide probes as optical signals.

An embodiment of the method of imaging a target within a living subject or a sample, among others, includes: introducing one or more quantum dots and one or more radionuclides into the living subject or sample; and detecting photons generated by one or a combination of the quantum dots and radionuclides, as an optical signal.

An embodiment of the system for imaging a target within a living subject or a sample, among others, includes: an optical detection system configured to detect low energy photons generated by one or more radionuclides as optical signals within said living subject or sample; and an optical signal processing system configured to provide images based upon the optical signal.

An embodiment of the system for analyzing an optical signal emitted by one or more radionuclides, among others, includes: detecting low energy photons generated by the one or more radionuclides as optical signals; and processing data corresponding to the detected optical signals to provide information about the optical signal emitted by the one or more radionuclides.

BRIEF DESCRIPTION OF THE DRAWINGS

Many aspects of the disclosed devices and methods can be better understood with reference to the following drawings. The components in the drawings are not necessarily to scale, emphasis instead being placed upon clearly illustrating the relevant principles. Moreover, in the drawings, like reference numerals designate corresponding parts throughout the several views.

The patent or application file contains at least one drawing executed in color. Copies of this patent or patent application publication with color drawing(s) will be provided by the Office upon request and payment of the necessary fee.

FIG. 1.1 illustrates that optical signals from radionuclides are detectable by OI instruments and have a continuous spectrum. FIG. 1.1(*a*) illustrates that most nuclides, except $^{99m}$Tc, provide OI signals with high sensitivity within as low as 0.004-0.370 MBq (0.1-10 µCi) range. ($^{18}$F: 5, 2, 1, 0.1 µCi; $^{131}$I: 10, 5, 1, 0.1 µCi; $^{90}$Y: 5, 1, 0.2, 0.01 µCi; $^{64}$Cu: 10, 5, 1, 0.1 µCi; $^{177}$Lu: 10, 5, 2, 0.5 µCi; $^{111}$In: 10, 5, 1, 0.5 µCi; $^{99m}$Tc: 20, 10, 5 µCi). FIG. 1.1(*b*) illustrates the detection sensitivity of different radionuclides. Radionuclides with a higher K value have stronger signal intensity. FIG. 1.1(*c*) illustrates the continuous spectra of different radionuclides. FIGS. 1.1(*d*) and (*e*) illustrate optical shielding tests of optical signals from radionuclides (FIG. 1.1(*d*)) and quantification analysis of imaging signals (FIG. 1.1(*e*)).

FIG. 1.2 illustrates phantom imaging studies with radioactive OI and PET. FIGS. 1.2(*a*) to 1.2(*c*) illustrate radioactive OI of $^{18}$F, $^{131}$I and $^{90}$Y phantoms. FIG. 1.2(*d*) illustrates PET imaging of the same $^{18}$F phantom in FIG. 1.2(*a*).

FIG. 1.3 illustrates in vivo radioactive OI of [$^{18}$F]FDG in comparison with microPET. FIG. 1.3(*a*) illustrates a bioluminescence image of a nude mouse bearing C6-fluc tumor. FIGS. 1.3(*b*) and (*c*) illustrate radioactive OI and microPET imaging of a nude mouse bearing C6-fluc tumor injected via tail vein with [$^{18}$F]FDG at 0.5, 1, 2 h p.i. FIGS. 1.3(*d*) and (*e*) illustrate radioactive OI of the mouse after opening the thorax (FIG. 1.3(*d*)) and exposure the organs (FIG. 1.3(*e*)) at 2.1 h p.i. FIGS. 1.3(*f*) to (*h*) illustrate quantitative analysis of radioactive OI (FIG. 1.3(*f*)) and microPET (FIG. 1.3(*g*)) results and their correlation (FIG. 1.3(*h*)).

FIG. 1.4 illustrates radioactive OI (FIG. 1.4(*a*)) and microPET imaging (FIG. 1.4(*b*)) of Na$^{18}$F at 0.5, 1, 2 h after i.v. injection.

FIG. 1.5 illustrates in vivo radioactive OI of Na$^{131}$I compared to SPECT/CT imaging. FIGS. 1.5(*a*) and (*b*) illustrate Coronal (FIG. 1.5(*a*)) and sagittal (FIG. 1.5(*b*))

images of SPECT/CT imaging at 1 h after injection of Na$^{131}$I probe. FIG. 1.5(c) illustrates radioactive OI of a normal mouse at 0.5, 1, 12, 24 h after injection of Na$^{131}$I via tail vein. FIG. 1.5(d) illustrates radioactive OI of a normal mouse after opening the thorax 24 h postinjection of Na$^{131}$I. FIG. 1.5(e) illustrates quantitative analysis (n=3) of thyroid uptake of Na$^{131}$I from radioactive OI results.

FIG. 1.6 illustrates in vivo radioactive OI of $^{90}$Y-RGD-BBN and $^{90}$YCl$_3$. FIGS. 1.6(a) and (b) illustrate radioactive OI (FIG. 1.6(a)) and quantitative analysis (n=3) (FIG. 1.6 (b)) of $^{90}$Y-RGD-BBN in mice bearing PC3 tumor. FIGS. 1.6(c) and (d) illustrate receptor blocking studies of $^{90}$Y-RGD-BBN probe using radioactive OI (FIG. 1.6(c)) and their quantification analysis (n=3) (FIGS. 1.6(d)). FIG. 1.6 (e) illustrates radioactive OI of $^{90}$YCl$_3$ at various time points p.i.

FIG. 2.1 illustrates in vitro cell imaging (FIGS. 2.1a, b, c) and sensitivity comparison studies of OI and PET (FIG. 2.1d). FIG. 2.1 illustrates: FIG. 2.1(a) C6 cell uptakes monitored by OI; quantification FIG. 2.1(b) and correlation FIG. 2.1(c) of C6 cell uptakes from both OI and gamma counting (GC) results; and FIG. 2.1(d) different radioactivity monitored by OI and PET [OI: 0.96, 0.60, 0.24 and 0.12 µCi (35.48, 22.18, 8.88 and 4.44 kBq); PET: 0.10, 0.06, 0.02 and 0.01 µCi (3.55, 2.22, 0.89 and 0.44 kBq)] (n=4).

FIG. 2.2 illustrates in vivo imaging using OI and PET. Mice bearing C6-tk and C6 tumors can be imaged by both OI (FIG. 2.2(a)) and PET (FIG. 2.2(b)). Statistical analysis (FIG. 2.2(c)) was performed for both modalities (n=6).

FIG. 2.3 illustrates biodistribution studies measured by OI (FIG. 2.3(a)) or gamma counting (FIG. 2.3(b)) at 1 h post-injection of [$^{18}$F]FHBG (n=6).

FIG. 3.1 illustrates IVIS-200 imaging system was modified to image phantom samples/animal subjects (denoted by "5"), pre-administered with $^{18}$F-FDG, using different optical fibers/endoscopes (OF). The subject "5" was placed outside the rectangular field of view (FOV) of the imaging system. The input end of the OF was placed close to the subject "5". The output end of the "OF" faced the CCD camera such that CCD camera was focused on the output end.

FIG. 3.2 illustrates the acceptance angle of a typical step index fiber with a fiber core of refractive index $n_1$ greater than refractive index $n_2$ of cladding. Light ray A outside the acceptance angle escapes into the cladding; Light ray B within the acceptance angle is guided through the fiber by total internal reflection and can therefore be detected by a CCD.

FIG. 3.3 illustrates a phantom sample containing about 10 µCi of $^{18}$F-FDG in 200 µL of PBS was imaged using different optical fibers and endoscopes with a one minute exposure time. Arrows indicate distal end of the instruments.

FIG. 3.4 illustrates the detection limits of various optical fibers. Luminescence detected by different fibers as a function of concentration of 18F-FDG with a 1 minute exposure time.

FIG. 3.5 illustrates in vivo animal imaging using 6 mm fiber optic bundle. Animals (n=4) bearing sub-cutaneous C6 glioma tumor is intravenously administered with 900 µCi $^{18}$F-FDG then sacrificed at one hour post injection for imaging.

FIG. 3.6(a) illustrates ex vivo radioactive optical imaging of different organs of an animal bearing C6 glioma tumor dissected after one hour post intravenous administration of 900 µCi $^{18}$F-FDG. Inset figure on top right corner of each organ represents average Cerenkov radiance detected by a 6 mm fiber optic bundle. FIG. 3.6(b) illustrates the biodistribution of $^{18}$F-FDG in various tissues at one hour post injection in mice as measured using radioactive optical imaging. Respective tissue optical signals from radioactive probes was measured by a 6 mm fiber optic bundle (n=4 for all organs). Bars represent the average tissue uptake plus/minus standard deviation (expressed as % injected dose/g of tissue).

FIG. 4.1 illustrates the radiation luminescence excited QDs for optical imaging.

FIG. 4.2 illustrates the spectroscopic characterization of radioactivity illuminated QDs. FIG. 4.2 (a) illustrates the absorption spectra of QD655, QD705 and QD800, and continuous emission spectra of $^{131}$I in phosphate buffered saline (PBS). FIG. 4.2(b) illustrates the emission spectra of QDs excited by radionuclide $^{131}$I (0.37 MBq). FIG. 4.2(c) illustrates the emission spectra of QDs illuminated by UV lights at 480 nm. D). Emission spectra of QDs excited by radionuclide $^{131}$I (0.37 MBq), after incubated with mouse serum for 1 h.

FIG. 4.3 illustrates in vivo radioactive optical imaging of Na$^{131}$I (0.37 MBq) and QD655 (8 pmol)/Na$^{131}$I (0.37 MBq) mixture. 1: Na$^{131}$I, subcutaneous injection; 2: QD655/Na$^{131}$I, subcutaneous injection; 3: Na$^{131}$I, intramuscular injection; 4: QD655/Na$^{131}$I, intramuscular injection. FIG. 4.3(a) illustrates imaging of the mouse with an open filter and optical lights was collected from 490 to 850 nm; FIG. 4.3(b) illustrates imaging of the same mouse with a filter and optical lights was collected from 575 to 650 nm; FIG. 4.3(c) illustrates fluorescence imaging of the same mouse with external UV light excitation at 500-550 nm.

FIG. 4.4 illustrates multiplexed in vitro radioactivity illuminated QD imaging. FIGS. 4.4(a) to (c) illustrate in vitro radioactivity illuminating spectral imaging of the QD655, QD705 and QD800, respectively. FIG. 4.4(d) illustrate spectral unmixed image of the same samples.

FIG. 4.5 illustrates multiplexed in vivo radioactivity illuminated QD imaging. FIGS. 4.5(a) to (c) illustrate in vivo radioactivity illuminating spectral imaging of the QD655, QD705 and QD800, separately. FIG. 4.5(d) illustrates spectral unmixed image of the same mouse as (FIGS. 4.5(a) to (c)).

DETAILED DESCRIPTION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of imaging, chemistry, synthetic organic chemistry, biochemistry, biology, molecular biology, microbiology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions

In describing and claiming the disclosed subject matter, the following terminology will be used in accordance with the definitions set forth below.

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art. As appropriate, procedures involving the use of commercially available kits and reagents are generally carried out in accordance with manufacturer defined protocols and/or parameters unless otherwise noted.

The term "molecular imaging", as used herein, relates to the in-vivo characterization and measurement of biologic processes and pathways at the cellular and molecular levels.

The term "optical imaging", as used herein, relates to the generation of images by using photons in a wavelength range (e.g., ultraviolet to infrared).

The term "resolution", as used herein, relates to the ability to distinguish two closely situated signals, structures or events accurately.

The term "spatial resolution", as used herein, relates to the ability to distinguish two closely situated signals or structures.

The term "temporal resolution", as used herein, relates to the ability to distinguish two closely occurring events in time.

The term "radioactive optical imaging", "radioactive molecular optical imaging", and "Cerenkov luminescence imaging" as used herein, relate to the detection of optical signals generated by radiolabelled or radioactive probes (also referred to as "radionuclide probes").

The terms "radionuclide probes", "radiolabelled probes" and "radioactive probes" have the same meaning and are used interchangeably.

The terms "radioactive optical imaging", "radioactive molecular optical imaging", and "Cerenkov luminescence imaging" have the same meaning and are used interchangeably.

The term "optical detection system", as used herein, can relate to fiber optic devices including, but not limited to, devices that can enhance emission/detection of weak light from emitters such as fluorophores, quantum dots, and radioactive substances, such as devices made of photonic crystal cavity. The term "optical detection system", as used herein, also includes endoscopes, including, but not limited to, endoscopes made of photonic crystal devices for enhanced detection of weak light emitted by radioactive probes administered into a living subject. The term "optical detection system", as used herein, also includes endoscopic cameras with or without the use of optic fibers.

The term "multiplexed detection", as used herein, relates to the simultaneous detection and differentiation of multiple wavelengths in the same sample.

The term "detectable" refers to the ability to detect a signal over the background signal.

The term "detectable signal" can refer to a signal derived from a radioactive substance, quantum dot, and the like. The detectable signal is detectable and distinguishable from other background signals that are generated from the subject or sample. In other words, there is a measurable and statistically significant difference (e.g., a statistically significant difference is enough of a difference to distinguish among the detectable signal and the background, such as about 0.1%, 1%, 3%, 5%, 10%, 15%, 20%, 25%, 30%, or 40% or more difference between the detectable signal and the background) between detectable signal and the background.

Standards and/or calibration curves can be used to determine the relative intensity of the detectable signal and/or the background.

The term "signal" as refers to a signal derived from a radioactive substance, a quantum dot, etc. is a signal that can be detected and quantitated with regards to its frequency and/or amplitude. The signal can be generated from one or more probes, quantum dots, or systems of the present disclosure. In an embodiment, the signal may need to be the sum of each of the individual signals. In an embodiment, the signal can be generated from a summation, an integration, or other mathematical process, formula, or algorithm, where the signal is from one or more probes, quantum dot, systems, or the like. In an embodiment, the summation, the integration, or other mathematical process, formula, or algorithm can be used to generate the signal so that the signal can be distinguished from background noise and the like. It should be noted that signals other than the signal of interest can be processed and/or obtained is a similar manner as that of the signal of interest.

The signal or energy can be detected and quantified in real time using an appropriate detection system such as those described herein.

The term "dispose" describes the permanent or temporary attachment of matter to a supporting material.

The term "in vivo imaging" as used herein refers to methods or processes in which the structural, functional, or physiological state of a living being is examinable without the need for a life ending sacrifice.

The term "non-invasive in vivo imaging" as used herein refers to methods or processes in which the structural, functional, or physiological state of a being is examinable by remote physical probing without the need for breaching the physical integrity of the outer (skin) or inner (accessible orifices) surfaces of the body.

The term "sample" can refer to a tissue sample, cell sample, a fluid sample, and the like. The sample may be taken from a subject. The tissue sample can include brain, hair (including roots), buccal swabs, blood, saliva, semen, muscle, or from any internal organs, or cancer, precancerous, or tumor cells associated with any one of these. The fluid may be, but is not limited to, urine, blood, ascites, pleural fluid, spinal fluid, and the like. The body tissue can include, but is not limited to, brain, skin, muscle, endometrial, uterine, and cervical tissue or cancer, precancerous, or tumor cells associated with any one of these. In an embodiment, the body tissue is brain tissue or a brain tumor or cancer.

The term "administration" refers to introducing a probe of the present disclosure into a subject. One preferred route of administration of the compound is oral administration. Another preferred route is intravenous administration. However, any route of administration, such as topical, subcutaneous, peritoneal, intraarterial, inhalation, vaginal, rectal, nasal, introduction into the cerebrospinal fluid, or instillation into body compartments can be used.

As used herein, the term "subject," or "patient," includes humans and mammals (e.g., mice, rats, pigs, cats, dogs, and horses). Typical subjects to which compounds of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living subject" refers to a subject noted above or another organism that is alive and not just a part excised (e.g., a liver or other organ) from the living subject.

General Discussion

Embodiments of the present disclosure provide for radionuclide probes, methods of using the radionuclide probes, methods of detecting an optical signal from radionuclides, methods of detecting an optical signal from a quantum dot(s) that receives optical energy from a radionuclide(s), systems for analyzing optical energy emitted by a radionuclide(s), systems for imaging a target within a living subject or a sample, methods of imaging a disease or condition, and the like. Embodiments of the present disclosure can be used to image, detect, study, monitor, and/or evaluate, a condition or disease such as, but not limited to, pre-cancerous tissue, cancer, or a tumor, in a subject or sample. In addition, embodiments of the present disclosure can be used for multiplexing systems.

In particular, exemplary embodiments of the present disclosure encompass methods and systems for non-invasive in-vivo optical molecular imaging using radiolabelled probes (e.g., radionuclide probes) that can provide high resolution images from a living subject or a sample. In addition, exemplary embodiments of the present disclosure provide methods and systems of medical imaging in the low energy window of light (<0.005 keV, at wavelengths >300 nm) generated by radionuclide probes, which should prove highly useful in preclinical and clinical diagnostics as well as prognostics and preclinical pharmaceutical research.

Light is electromagnetic radiation, particularly radiation of a wavelength that is visible to the human eye (e.g., about 350-750 nm). Radionuclides, including alpha and beta emitters, are able to generate continuous spectra of photons by interaction with surrounding materials and therefore, can be monitored at different wavelengths. The lower energy photons associated with emitted charged particles during decay of radionuclides, corresponding to an energy below 0.005 keV and to wavelengths above about 300 nm, have been found to be highly suited for medical molecular imaging due to the achieved high sensitivity and spatial resolution.

Compared to conventional fluorescence and bioluminescence imaging, radioactive optical imaging (OI) has some unique properties. The continued emission wavelength of radioactive OI allows monitoring and imaging of a radionuclide at different wavelengths, which is a significant advantage over the conventional optical imaging modalities. And the radioactive OI signal generated by a radionuclide does not require an excitation light and is always on, which is different from fluorescence and bioluminescence probes, which typically need an outside source of energy and which may produce unwanted and complicating optical signals from other sources (e.g., skin). In an embodiment, the optical signal can be used to excite a quantum dot so the quantum dot can emit energy without the requirement of an excitation light.

As mentioned above, an exemplary embodiment of the present disclosure includes a method of imaging a target within a living subject (e.g., mammal such as a human) or a sample (e.g., tissue, organ, and the like). Initially, one or more (e.g., amount and/or type) radionuclides (e.g., radionuclide probes) are introduced into the living subject or sample. Subsequently, low energy photons generated by the one or more radionuclide probes are detected as an optical signal(s).

In an embodiment, the radionuclide can include radionuclides except those that are pure gamma rays-emitting radionuclides. In particular, the radionuclides can include those that emit radionuclides that are α, β⁺, β⁻-emitters. Specifically, the radionuclide can include the following: $^{11}$C, $^{13}$N, $^{15}$O, $^{18}$F, $^{68}$Ga $^{131}$I, $^{90}$Y, $^{177}$Lu, $^{123}$I, $^{111}$In, $^{211}$At, $^{212}$Bi, $^{213}$Bi, $^{223}$Ra, $^{225}$Ac, $^{67}$Cu, $^{111}$Ag, $^{131}$I, $^{149}$Pm, $^{153}$Sm, $^{166}$Ho, $^{177}$Lu, $^{186}$Re, $^{188}$Re, $^{211}$At, $^{212}$Bi, and $^{223}$Ra. In an embodiment, the wavelength emitted by the radionuclides is in the visible or infrared or a combination thereof, i.e., energy of light about 0.005 keV or less, at wavelengths of about 300 nm or more.

In an exemplary embodiment, the radionuclide is included in a radionuclide probe. The radionuclide can be bonded to the probe. In an embodiment, the probe can include, but is not limited to, a drug, a therapeutic agent, a radiological agent, a chemological agent, a small molecule drug, a biological agent (e.g., peptides, proteins, polynucleotides, DNA, RNA, antibodies, antigens, and the like), or a combination thereof, that is attached to the radionuclide. In an embodiment, the probe can inherently have an affinity (e.g., preferentially be attracted to and/or bind or exclusively attracted to and/or bind) for a target(s) that may be present in the living subject or the sample. In an embodiment, the probe can include a targeting agent that has an affinity for the target(s). In an embodiment, both the probe and the targeting agent can have an affinity for the same or different targets.

In an embodiment, the targeting agent can function to cause the probe to interact (e.g., be attracted to, bond, and the like) with a target (e.g., a molecule(s)). In an embodiment, the targeting agent can have an affinity for a cell, a tissue, a protein, DNA, RNA, an antibody, an antigen, a compound, and the like, that may be associated with a condition, disease, or related biological event, of interest. In particular, the targeting agent can function to target specific DNA, RNA, and/or proteins of interest. In an embodiment, the targeting agent can include, but is not limited to, polypeptides (e.g., proteins such as, but not limited to, antibodies (monoclonal or polyclonal)), antigens, nucleic acids (both monomeric and oligomeric), polysaccharides, sugars, fatty acids, steroids, purines, pyrimidines, ligands, aptamers, small molecules, ligands, or combinations thereof, that have an affinity for a condition, disease, or related biological event or other chemical, biochemical, and/or biological events of the condition, disease, or biological event. In an embodiment, the targeting agent can include: sequence-specific DNA oligonucleotides, locked nucleic acids (LNA), and peptide nucleic acids (PNA), antibodies, and small molecule protein receptors.

In an exemplary embodiment, the condition or disease can be associated with a cellular abnormality. In an embodiment, the condition or disease can be selected from the group consisting of: cancer, inflammatory disease, immunological disease, neurodegenerative disease, cardiovascular disease, and an infectious disease. In an embodiment, the cancer, precancerous tissue or cells, or tumor that is associated with one or more of the following: breast cancer, ovarian cancer, cervical cancer, pancreas cancer, colorectal cancer, prostate cancer, lung cancer, brain tumor, skin cancer, gastrointestinal cancer, esophageal cancer, mouth cancer, bone cancer, or renal cancer. In an embodiment, the cancer, precancerous tissue or cells, or tumor that is associated with one or more of the following: colon, lung, bronchi, breast, thyroid, pancreas, kidneys, ovaries, cervix, prostate, brain, skin, gastrointestinal tract, esophagus, mouth, or bone tissue.

After the optical signal corresponding to the radionuclide is obtained corresponding to the radionuclide, the optical signal or data corresponding to the detected optical signal can be processed to provide an image of the target or the area where the target is located. In an embodiment, the image can be a planar image or can be a 3-dimensional image of the target. In particular, the optical signal can be used to identify an area from which the optical signal is produced, where the area corresponds to the location of the target.

Once the optical signal corresponding to the radionuclide is obtained, the status of the condition or disease can be evaluated or monitored by comparing the image with one or more previous images and one or more subsequent images.

Embodiments of the present disclosure also enable determining pharmacokinetic parameters of an experimental or pharmacological molecule in the living subject or the sample. In an embodiment, by sequentially imaging the same target after injection of radioactive agents, the uptake changes in the living subject can be monitored. The uptake changes are reflected by the strength of the optical signals.

In another embodiment, a method includes imaging reporter gene expression within a living subject or cells, whereby one or more radionuclides are introduced into the living subject or cells and the resulting low energy photons are detected as optical signals in the visible or infrared range. The optical signals are then processed to determine protein expression, protein function and/or protein-protein interaction in the living subject or cells. Molecular imaging modalities provide much needed relevant molecular, biological and biochemical information by visualizing and quantitating relevant molecular and physiological variables, that might be the cause or a contributing factor to human disease, such as altered cellular metabolism, cellular proliferation, perfusion, gene expression, protein-protein interaction, receptor density and enzymatic expression. Molecular imaging modalities are also instrumental in monitoring molecular events during treatment to determine treatment success and to obtain prognostic information as well as after treatment to detect disease recurrence.

Embodiments of the present disclosure also enable real-time monitoring of surgery at a surgical region of interest that may include the target.

Beta emitters (positron/β⁺ and electron/β⁻)-based molecular probes were tested in living mice using a commercial available optical imaging instrument with a charge-coupled device (CCD) camera (IVIS Spectrum, Caliper). High quality in-vivo optical images with high spatial resolution were obtained for several radioactive probes such as 2-deoxy-2-[$^{18}$F]fluoro-D-glucose ([$^{18}$F]FDG), Na$^{18}$F, Na$^{131}$I, $^{90}$YCl$_3$ and a $^{90}$Y labeled tumor targeting peptide, which illustrates the feasibility of molecular imaging of living subjects using optical imaging modalities in conjunction with radioactive probes. Additional details are provided in the Examples.

As mentioned above, an exemplary embodiment of the present disclosure includes a method of imaging a target within a living subject (e.g., mammal such as a human) or a sample (e.g., tissue, organ, and the like) using a radionuclide and a quantum dot. Initially, one or more (e.g., amount and/or type) radionuclides (e.g., radionuclide probes) and one or more quantum dots (e.g., amount and/or type) are introduced into the living subject or sample. Subsequently, low energy photons generated by the one or more radionuclide probes are detected as an optical signal(s) and/or the quantum dot absorbs the energy from the radionuclide and then the quantum dot emits an optical signal. It is advantageous for the quantum dots to absorb energy from the radionuclide so that an outside energy source is not needed to excite the quantum dots, since the outside or external energy source can also cause other background signals (e.g., optical signals) to be generated, thereby interfering with the optical signal of interest. Thus, in an embodiment, the method or system used does not need the use of an external, outside, or another source of energy to excite the quantum dots since the radionuclides excite the quantum dot.

In an embodiment, the quantum dot and the radionuclide are included in separate species (e.g., a quantum dot probe and a radionuclide probe respectively). The radionuclide probe can include those described herein. The quantum dot probe can include another of the probes described in reference to the radionuclide probe, where the quantum dot is associated with (e.g., bonded, form a complex with, and the like) the probe. The quantum dot probe and the radionuclide probe can be designed to have an affinity towards the same target or similar target. Thus, if the quantum dot and the radionuclide are present at the area of the target, the quantum dot should emit energy associated with an optical signal that corresponds to the quantum dot. The various optical signals can be separated based on wavelength and/or intensity to determine the area where the optical signal from the quantum dot is derived.

In an embodiment, the radionuclide probe can optionally include the quantum dot. The quantum dot can be associated with (e.g., bonded, form a complex with, and the like) the probe directly or indirectly (e.g., via a chemical or biochemical linking group of compound), many of which are known in the art. In an embodiment, the quantum dot and radionuclide can be positioned so that the optical energy emitted from the radionuclide is maximized. In an embodiment, the probe can be configured that upon interaction with the target, the probe undergoes a change so that the quantum dot and the radionuclide are brought into proximity to maximize the energy emitted by the quantum dot. As described above with regard to radionuclides, the radionuclide probe including the quantum dot can have an affinity for one or more targets. Measuring an optical signal corresponding to the quantum dot that is concentrated in a specific area or location is indicative that the target is present at the location of the origin of the optical signal.

After the optical signal corresponding to the quantum dot (and/or the radionuclide) is obtained, the optical signal or data corresponding to the detected optical signal can be processed to provide an image of the target. In an embodiment, the image can be a planar image or can be a 3-dimensional image of the target. In particular, the optical signal can be used to identify an area from which the optical signal is produced, where the area corresponds to the target.

Once the optical signal corresponding to the quantum dot (and/or the radionuclide) is obtained, the status of the condition or disease can be evaluated or monitored by comparing the image with one or more previous images and one or more subsequent images.

Embodiments of the present disclosure also enable determining pharmacokinetic parameters of an experimental or pharmacological molecule in the living subject or the sample. Embodiments of the present disclosure also enable real-time monitoring of surgery at a surgical region of interest that may include the target. In another embodiment, a method includes imaging reporter gene expression within a living subject or cells, whereby one or more radionuclides are introduced into the living subject or cells and the resulting low energy photons are detected as optical signals in the visible or infrared range. The optical signals are then processed to determine protein expression, protein function and/or protein-protein interaction in the living subject or cells.

The term "quantum dot" (QD) refers to semiconductor or insulator nanoparticle with or without one or more dopants. QDs may also be known as nanocrystals, or artificial atoms, which are crystals that contain anywhere between about 100 to 500,000 atoms and have a diameter of about 1-250 nm in diameter (or length of the longest dimension), with spherical or more complex shapes such as platelets, faceted particles, cylinders, and the like.

In an embodiment, the QD is a luminescent semiconductor QDs. Semiconductor QDs are fluorophores that fluoresce by forming excitons, which can be thought of as the excited state of traditional fluorophores, but may have much longer lifetimes of up to about 200 nanoseconds.

In general, a QD can include a core material and a capping (also called a shell) material, however, an uncapped QD can be used as well. In an embodiment, the "core" is a semiconductor or doped or undoped insulator nanoparticle with dimensions of about 1 to 250 nm. While any core of the IIB-VIA, IIIA-VA, or IVA-IVA, IVA-VIA, IB-IIIA-VIA semiconductors or doped or undoped insulator can be used in the context of the present disclosure, the core may be a luminescent QD, whose luminance may be increased by a capping layer. A IIB-VIA semiconductor is a compound that contains at least one element from Group IIB and at least one element from Group VIA of the periodic table, and so on. The core can include two or more elements. In an embodiment, the core of the QD can also be a transition metal oxide or lanthanide metal oxide QD doped with rare earth or transition metal ions, or a combination thereof. In another embodiment, the core of the QD is a Group IA or IIA or solid solutions between Group IA elements, Group IIA elements, and combination thereof, or lanthanide metals bound to a Group VIIA halide with or without a dopant, particularly rare earth ions and transition metal ions, Ce-doped Lu, Y and Gd oxyorthosilicates, Ce-doped oxyorthosilicates made with a combination of at least two of the elements Y, Lu and Gd, Ce-doped Sr or Ba hafanate, or alloys. In one embodiment, the core is an IIB-VIA, IIIA-VA, or IVA-IVA semiconductor. In an embodiment, the core can be about 1 nm to 40 nm, about 1 nm to 30 nm, about 1 nm to 20 nm, or about 1 nm to 10 nm in diameter. In another embodiment, the core can be an IIB-VIA semiconductor and can be about 2 nm to 10 nm in diameter. For example, the core can be CdS, CdSe, CdTe, ZnSe, ZnS, ZnS:Ag, ZnO:Ag, PbS, PbSe, or an alloy.

The "cap" or "shell" may be a semiconductor or insulator that differs from or is the same as the semiconductor or insulator of the core and binds to the core, thereby forming a surface layer on the core. A shell can differ from the core and/or other shells by means of its chemical composition, and/or the presence of one or more dopants, and/or different amounts of a given dopant. The shell typically passivates the core by having a higher band gap than the core, and having an energy offset in the top of the valence band and bottom of the conduction band such that electrons and/or holes may be confined to the core by the shell. In one embodiment, the shell can be a IIB-VIA semiconductor of high band gap. For example, the shell can be ZnS or CdS on a core of $CdSe_yTe_{1-y}$ (y is variable from about one to zero). Other combinations of the core and shell can include, but are not limited to, the shell is ZnS when the core is CdSe or CdS, and the shell is CdS when the core is CdSe. Other exemplary QDs include, but are not limited to, CdS, ZnSe, ZnS:Ag, ZnO:Ag, CdSe, CdTe, InAs, InP, PbTe, PbSe, PbS, HgS, HgSe, HgTe, CdHgTe, and GaAs. In an embodiment, the thickness of the shell can be about 0.1 to 20 nm, about 0.1 to 5 nm, or about 0.1 to 2 nm covering the core. In an embodiment, the shell is CdSe. The shells can be of doped or undoped insulators, or a combination of semiconductor and doped and undoped insulators, including, but not limited to, $CeF_3$, $CeBr_3$, $LaBr_3$, $CaF_2:Eu$, $BaF_2:Ce$, $LaF_3$ doped with one or more lanthanide ions, Ce-doped Lu, Y and Gd oxyorthosilicates, or Ce-doped oxyorthosilicates made with a combination of at least two of the elements Y, Lu and Gd, Ce-doped Sr or Ba hafanate, or alloys. The core may also be a transition metal or lanthanide metal oxide, nitride, halide, or oxynitride.

The wavelength of the light emitted (e.g., color) by the QDs can be selected according to the physical properties of the QD, such as the size, the material of the nanocrystal, and the dopant. Nanoparticles are known to emit light from about 200 nanometers (nm) to 2000 nm (e.g., UV, visible, near IR, and IR). The colors of the nanoparticles include, but are not limited to, red, blue, violet, green, and combinations thereof. The color or the fluorescence emission wavelength of semiconductor QDs with a size less than the Bohr radius can be tuned continuously. The wavelength band of light emitted by the QD may be determined by either the size of the core or the size of the core and shell, depending on the materials that make up the core and shell. The emission wavelength band can be tuned by varying the composition and the size of the QD and the like. In the case of doped insulators, the color of emitted light is generally independent of the size of the quantum dot, and is mostly related to the nature of the dopant and host. However the excitation wavelength for photoluminescence may depend upon the size of the quantum dot.

As noted above, embodiments of the present disclosure include a system for imaging a target within a living subject or a sample. In an embodiment, the system can include an optical detection system and an optical signal processing system. In an embodiment, the optical detection system can be configured to detect low energy photons generated by one or more radionuclides as optical signals within the living subject or sample. In an embodiment, the optical signal processing system is configured to provide images based upon the optical signal. As described above, the optical signal can be processed to produce an image. As described herein, the location of the target can be obtained using the optical data or information corresponding to the optical signal. Additional details are provided in the Examples.

In an embodiment, the optical detection system can include an endoscope (e.g., arthroscope, bronchoscope, cystoscope, laparoscope, and the like, depending upon the procedure) that can be in communication with an optical signal processing system. In an embodiment, the optical detection system (e.g., endoscope) can include one or more optical fibers and/or photonic devices, and optionally optical focusing or collecting devices, to detect and/or to transmit low energy photons generated by one or more radionuclide as optical signals and/or optical signals from a quantum dot. In an embodiment, the tip of the optical detection system, an endoscope for example, can be positioned in close proximity to detect optical signals to an area of interest (e.g., tissue) and moved accordingly to survey a larger area of interest (e.g., the colon).

In an embodiment, the system can be an optical in vivo imaging system that can be used to visualize molecular events in an organism by detecting emitted photons. In an embodiment, the optical detection system includes an optical fiber system (e.g., optical fiber, optics for focusing and or direction the optical energy). The optical signal is directed using the optical fiber system to a charge-coupled device camera (CCD camera) that are often utilized for capturing images and converting them into digital values to produce an image.

Embodiments of the methods and systems of the present disclosure can be used in preclinical pharmaceutical research/whole-body biodistribution kinetics. Molecular imaging of a living subject allows the temporal and spatial visualization of the biodistribution of a molecule and related biological processes to be determined in real time and noninvasively. Imaging in large and/or small animals provides a bridge from animal research to human research and the clinic, validating and enabling similar and sometimes identical experiments to be carried out across species. Much of the technology development in imaging is now directed at small laboratory animals such as rats and mice. However, larger laboratory animals such as dogs, pigs, and nonhuman primates continue to play an important role in studies of the central nervous system and the heart.

Embodiments of the methods and systems of the present disclosure may be useful for diagnosing, prognosis, staging and monitoring the progression, remission and recurrence of cancers and many other diseases and are expected to be widely adopted due to the higher sensitivity achieved, higher throughput, lower cost and broader user accessibility when compared to conventional nuclear-based imaging techniques such as positron emission tomography (PET) or single photon emission tomography (SPECT). The use of radionuclides for optical imaging, as described in embodiments of the present disclosure, is expected to have a major impact on the molecular imaging field.

So far, radioactive agents have traditionally been studied by PET, SPECT or γcameras; however, these scanners and detectors are expensive, hard to maintain and not widely available to many researchers. Embodiments of the present disclosure show that commercial available optical imaging instruments can, apart from bioluminescence and fluorescence imaging, be used for studying radioactive probes including alpha/α, positron/$β^+$ and electron/$β^-$ radionuclides. Considering the much lower capital and maintenance costs and wider accessibility of the optical imaging instruments compared to PET, SPECT or γ cameras, developing radioactive probes will likely be dramatically accelerated by using the described approach of radioactive optical imaging.

Embodiments of the methods and systems of the present disclosure may be useful for radioactive optical imaging in cancer imaging and in imaging of other diseases. Radioactive optical imaging can be used in the detection, characterization and/or determination of the localization of a disease ranging from early to late stage disease. Radioactive optical imaging has, furthermore, utility in staging a disease, i.e., determining the severity of a disease, monitoring the progression (worsening) of a disease, and/or monitoring the regression (improvement) of a disease, for example through imaging protein expression, protein function and protein-protein interaction on a molecular level (reporter gene technology). Radioactive optical imaging can also be used in the prognosis of a disease or disease conditions. Radioactive optical imaging could be very useful for cancer imaging, in particular for imaging of solid cancers including breast cancer, ovarian cancer, cervical cancer, pancreas cancer, colorectal cancer, prostate cancer, lung cancer, brain tumor, skin cancer, gastrointestinal cancer, esophageal cancer, mouth cancer, or bone cancer, including metastases.

In addition, radioactive optical imaging has further utility in imaging diseases that are characterized by inflammation processes such as rheumatoid arthritis, whereby the presence and location of inflammation can be imaged; cardiovascular diseases including atherosclerosis, ischemia, stroke, or thromboses, whereby plaques, areas at risk for acute occlusion as well as areas of hypoxia can be imaged; infectious diseases, whereby areas inflicted with bacterial, viral, fungal, parasitic pathogens can be imaged. Radioactive optical imaging might also be useful for imaging immune cells to aid diagnosing immunological diseases and for neuroimaging to aid diagnosing neurodegenerative diseases.

As described herein a wide range of radiolabelled probes can be used in the methods and systems of the present disclosure. In embodiments of the present disclosure, isotopes that are pure beta-emitters such as $^{90}Y$ can be utilized, in contrast to gamma-rays-emission based imaging modalities such as PET or SPECT. Beta-particles, i.e. electrons, do not travel significant distances in tissue and do not produce gamma rays through annihilation events, as positrons do; therefore, pure beta-emitters cannot be utilized for imaging modalities such as PET or SPECT. Radionuclide ($\alpha$, $\beta^+$, $\beta^-$, electron capture, etc.) that emit charged particles are likely suitable for optical imaging.

Molecular imaging modalities such as those described herein provide much needed relevant molecular, biological and biochemical information by visualizing and quantitating relevant molecular and physiological variables, that might be the cause or a contributing factor to human disease, such as altered cellular metabolism, cellular proliferation, perfusion, gene expression, protein-protein interaction, receptor density and enzymatic expression. Molecular imaging modalities such as those described herein are also instrumental in monitoring molecular events during treatment to determine treatment success and to obtain prognostic information as well as after treatment to detect disease recurrence.

Optical techniques are, in contrast to the non-optical techniques, generally less expensive due to lower capital and maintenance expenses, are easier to perform and often allow a straight forward interpretation of the results. Furthermore, optical imaging instruments allow, in comparison to imaging scanners such as PET or SPECT, a higher throughput. Thus, using optical imaging with radionuclides is advantageous relative to some other techniques.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

Molecular imaging is a relatively new and fast growing research discipline, which has the ability to study diseases non-invasively in living subjects at the molecular level[1-4]. Numerous researches have demonstrated that molecular imaging techniques play a central role in the era of personalized medicine. A variety of imaging modalities have been developed for providing functional and anatomical information of diseases in living small animals and patients, which include positron emission tomography (PET), single photon emission computed tomography (SPECT), optical imaging (OI, bioluminescence and fluorescence), magnetic resonance imaging (MRI), ultrasound (US), and computed tomography (CT), etc[1,2].

Radioactive molecular probes are traditionally imaged with PET, SPECT or gamma ($\gamma$) cameras, by taking advantages of the capability of these imaging modalities to detect the high energetic $\gamma$ rays. Whereas OI generally detects low energy lights (visible or near-infrared lights) emitted from bioluminescence or fluorescence probes[1]. So far there has not been any overlap between radioactive probes and conventional OI techniques.

In this research, we hypothesized that radiation from radionuclides in the low energy window of light (1.2-3.1 eV, 400-1000 nm) could be especially useful for molecular OI. Beta emitters ($\beta^+$ and $\beta^-$) based molecular probes were then tested in mice using a commercial available OI instrument (IVIS Spectrum, Caliper). High quality of in vivo optical images were obtained for several radioactive probes such as 2-deoxy-2-[$^{18}F$]fluoro-D-glucose ([$^{18}F$]FDG), Na$^{18}F$, Na$^{131}I$, $^{90}YCl_3$, and a $^{90}Y$ labeled tumor targeting peptide. The results presented here for the first time bridge the radioactive probes and OI. It demonstrates the feasibility of molecular imaging of living subjects using OI modalities in conjunction with radioactive probes.

Results

Optical Signals from Radioactive Probes can be Used for OI

In order to determine whether radioactive material could be used for OI, we first tested a variety of radionuclides with different amount of radioactivity using an IVIS Spectrum OI system. These radionuclides included $\beta^+$ emitters ($^{18}F$ and $^{64}Cu$), $\beta^-$ emitters ($^{131}I$, $^{90}Y$, and $^{177}Lu$), and $\gamma$ emitters ($^{111}In$ and $^{99m}Tc$). It was found that the majority of radionuclides, except $^{99m}Tc$, did provide optical signals with good sensitivities within a 1-5 min imaging time (FIG. 1.1a). This encouraging result clearly verified our hypothesis. Under the condition used in the studies, good signal-to-background (S/N) (>20 or 7 for $^{18}F$ or $^{131}I$, respectively) could be observed with even 0.1 µCi of radioactivity for both $^{18}F$ and $^{131}I$, while 0.01 µCi of $^{90}Y$ could still be detected with a S/N over 6. The OI intensity vs radioactivity was then plotted for these radionuclides (FIG. 1.1b). The K values of the slopes for different radionuclides indicate their imaging sensitivity. Obviously, the pure $\beta^-$ emitter $^{90}Y$ has the highest sensitivity among all the radionuclides evaluated, and the detection sensitivity of the $^{18}F$ and $^{131}I$ was ranked as $2^{nd}$ and $3^{rd}$, respectively. Finally, the pure $\gamma$ emitter $^{99m}Tc$ was undetectable even when high radioactivity (20 µCi) was applied, suggesting the OI signal was not caused by $\gamma$ rays (FIG. 1.1a).

IVIS Spectrum system also renders us ability to measure the OI imaging signal intensities at different wavelengths (from 490 to 850 nm). It was found that the total OI signals produced by these radionuclides were actually contributed by lights at different wavelengths monitored by the instrument (490-850 nm), which was in consistence with the nature of the continued spectrum of Cerenkov or Bremsstrahlung radiation. For the radionuclides tested, the percentages of optical signal intensity at different wavelengths vs. wavelength were shown in FIG. 1.1c. All of these radionuclides shared a similar distribution pattern, indicating the same mechanism for light producing. High light intensity was observed at 490-540 nm, the light intensity was then slowly reduced at 540-700 nm, and then it remained plateau at 700-850 nm (FIG. 1.1c). To further demonstrate that OI signals were attributed to the optical signals from radioactive probes, instead of $\beta$ particles or $\gamma$ radiation directly, white and black papers were used to cover the surface of the radioactive samples. It was found that the light signal could be significantly blocked by the coverage of a piece of white or black paper, and black paper also showed better OI signal shielding ability than white paper (FIG. 1.1d and 1.1e).

Phantom Imaging Study

To further explore the potential of using optical signals from radioactive probes for OI, phantom imaging study was performed to determine the detection spatial resolutions of three most sensitive radionuclides studied ($^{18}$F, $^{131}$I and $^{90}$Y) in the IVIS Spectrum system (FIG. 1.2). The radioactive OI showed that 1.2 mm spatial resolution could be achieved for all three radionuclides (FIG. 1.2a, 1.2b and 1.2c). For comparison, $^{18}$F-microPET imaging study (FIG. 1.2d) (Siemens microPET R4 rodent model scanner) revealed that the spatial resolution for the same $^{18}$F phantom was ~2.4 mm. The detection resolution reported for SPECT radionuclides is in 1-2 mm[1], and pure β$^-$ emitter $^{90}$Y has very poor resolution (in cm range) when SPECT or γ cameras was used for imaging its high energy bremsstrahlung radiation[7-12]. Overall, the results of phantom study clearly demonstrated that the optical signals from radioactive probes could be used for living subject imaging because of its high spatial resolution.

In Vivo Radioactive OI with a β$^+$ Emitter, $^{18}$F

The optical signals from radioactive probes for in vivo molecular imaging was first demonstrated by using two well-known PET probes, 2-deoxy-2-[$^{18}$F]-fluoro-D-glucose ([$^{18}$F]FDG) and Na$^{18}$F. [$^{18}$F]FDG has been widely used for imaging tumor metabolism[2,13,14], and Na$^{18}$F can accumulate in the bone[14]. In this study, a group of mice (n=3) were implanted with firefly luciferase (fluc) transfected rat C6 glioma (C6-fluc). A day prior to the radioactive imaging, the mice were given with luciferin and bioluminescence OI was performed to verify the presence of tumor (FIG. 1.3a). Then [$^{18}$F]FDG was injected to the mice bearing C6-fluc glioma and imaged sequentially with IVIS Spectrum (FIG. 1.3b) and microPET (FIG. 1.3c). [$^{18}$F]FDG preferentially localized and was retained in C6-fluc tumors, as clearly shown in both radioactive OI and microPET imaging technique (FIG. 1.3b and 1.3c). High imaging signals from bladder and brain were also observed by both modalities. But heart was hardly visible in the radioactive OI because it localizes deep inside of the mice body. After we sacrificed and open the thorax of the mice, the heart could be easily identified (FIG. 1.3d, yellow arrow). To further characterize the distribution of [$^{18}$F]FDG using radioactive OI, tumors and other normal organs and tissues were removed from the mice sacrificed and subjected to IVIS Spectrum imaging. High activity was mainly observed from the tumor and heart tissue samples (FIG. 1.3e).

Quantitative analysis of both radioactive OI and microPET images was performed. The OI intensities in the tumor and the normal tissue as a function of time for [$^{18}$F]FDG was depicted in FIG. 1.3f, while the radioactivity accumulation in tumor and muscle over time was shown in FIG. 1.3g. It was found that radioactive OI and microPET imaging provided similar information regards of the [$^{18}$F]FDG uptake and kinetic in tumor and muscle (FIG. 1.3f and 1.3g). The tumor uptake of [$^{18}$F]FDG increased over time (from 0.5-2 h) but with no significant difference (P<0.05). Finally, regression analysis was performed for the tumor uptakes obtained from two imaging modalities, in order to further evaluate the quantitative analysis data obtained from radioactive OI. Good correlation was seen between the radioactive OI signal intensities and microPET images derived tumor uptakes (FIG. 1.3h, $r^2$ over 0.90 for the analyses). This result illustrated that radioactive OI had value to serve as a promising tool for semi-quantitative analysis of the biodistribution of a radioactive probe.

Bone-seeking PET probe, Na$^{18}$F, was also used for radioactive OI and microPET imaging studies to further confirm the use of optical signals from radioactive probes for molecular imaging. High and consistence imaging signals were observed in the bone structures (vertebral column, cranium, etc.) in both imaging modalities (FIG. 1.4a and 1.4b).

Radioactive OI with a β$^-$ Emitter, $^{131}$I

Iodine ion can accumulate in the thyroid, and Na$^{123/131}$I has been widely used for imaging thyroid function, treating thyroid cancer and sodium iodide symporter[15-17]. Therefore, we then tested the SPECT probe, Na$^{131}$I, for thyroid radioactive OI. Na$^{131}$I SPECT/CT fusion images shown in FIG. 1.5a (coronal image) and 1.5b (sagittal image) clearly displayed the mouse bone anatomic structure (brown-red color) and the localization of the probe in the thyroid and abdomen region (green color, thyroid was indicated by an arrow). On the other hand, radioactive OI showed similar finding. High imaging signal was found in the thyroid and bladder at earlier time points postinjection (p.i.). The thyroid activity slowly increased, while the activity in the bladder was cleared out at later time points (FIG. 1.5c). At the end of OI study, the mice were sacrificed and the neck and chest areas were opened to expose the internal organs. The thyroid can be easily differentiated (FIG. 1.5d). Quantitative analysis of OI demonstrated that Na$^{131}$I accumulated and maintained in the thyroid (FIG. 1.5e).

Radioactive OI with a Pure β$^-$ Emitter, $^{90}$Y

Arg-Gly-Asp (RGD) coupled with bombesin (BBN) peptide (RGD-BBN) analogs were recently reported as heterodimeric peptides for dual targeting of integrin $α_vβ_3$ and gastrin-releasing peptide receptor (GRPR). Radiolabeled ($^{64}$Cu, $^{18}$F, $^{68}$Ga, etc.) RGD-BBN peptides have been reported for successfully PET imaging of human prostate cancer in a PC3 tumor mice model[18-20]. We labeled 1,4,7,10-tetraazacyclododecane-1,4,7,10-tetraacetic acid (DOTA) conjugated RGD-BBN with $^{90}$Y and tested $^{90}$Y-DOTA-RGD-BBN for radioactive OI. As shown in FIG. 1.6a, PC3 tumors were visible especially at 1 and 4 h p.i., with good tumor-to-background contrast. Also observed was a high accumulation of activity in the kidneys for the probe at 0.2 h p.i., while high bladder activity was observed at 0.5 and 1 h p.i. (FIG. 1.6a). For mice co-injected with a large excess of RGD and BBN peptides, the tumors were hardly visible on optical images at 60 min p.i. (FIG. 1.6c). Quantification analysis of optical images showed the kinetic of tumor targeting (FIG. 1.6b) and much lower tumor uptake for blocking mice than that of nonblocked mice (P<0.05) (FIG. 1.6d).

Mice injected with $^{90}$YCl$_3$ (1.8-2.0 MBq each) were also imaged by an IVIS Spectrum system at different time points p.i. (FIG. 1.6e). It could be clearly seen that $^{90}$Y accumulated in the liver as well as in the bone (femur). High activity in the bladder suggested the clearance route of this agent. The results obtained by the radioactive OI also agreed well with the previously reports which measured the in vivo behavior of $^{90}$YCl$_3$ by biodistribution study[21].

Discussion

Developing novel imaging techniques and instruments has been a major effort in the molecular imaging field. OI is a new rising technique with many advantages such as high sensitivity, low-cost, easy to use, relative high-throughput, quick imaging time, etc[1]. Recent advance in optical imaging instruments and molecular probes have made it an excellent tool in small animal research as well as potential use in patients' management. In this research, to the best of our knowledge, we for the first time demonstrate that OI techniques can also be used to image visible and near-infrared lights produced by radioactive material. This finding made OI a modality of choice for evaluation of bioluminescent, fluorescent and radioactive probes.

The success of using radionuclides for OI as demonstrated here is expected to have a major impact to the molecular imaging field. First, radioactive agents are traditionally studied by PET, SPECT or γ cameras, which are expensive, hard to maintain and not widely available to many researchers. Our results clearly show that the commercial available OI instrument can be used for studying radioactive probes including both $\beta^+$ and $\beta^-$ radionuclides, besides its ability for bioluminescence and fluorescence imaging. Considering the much lower cost and wider accessibility of the OI instruments than that of PET and SPECT, developing radioactive probes will likely be dramatically accelerated by using radioactive OI strategy. Second, IVIS system can image up to five animals simultaneously, while small animal PET and SPECT only image a mouse at one time. The high throughput manner of OI equipments will also help to improve the speed of radioactive probe development. Third, although OI is an important tool in animal research, its clinical applications have been severely hampered by very limited OI probes approved by the Food and Drug Administration (FDA). So far only iodocyanine green dye (IC-Green) has been used in human[22]. While radioactive imaging have a longer history in biomedical imaging and have been widely used in clinic for the past several decades. Many FDA approved SPECT and PET probes including [$^{18}$F]FDG have been developed for imaging different diseases and molecular targets. New applications of these radioactive probes may be developed in conjunction with radioactive OI techniques. This really highlights the strong clinic translational ability of our discovery. The research presented here opens a new avenue for small animal imaging research, as well as for imaging patients in clinic with these radioactive probes coupled with different optical imaging instruments and techniques.

Three radionuclides ($^{18}$F, $^{131}$I, and $^{90}$Y) were evaluated in small animal radioactive OI in this research, because of their important role in nuclear medicine. $^{18}$F is the most often used PET radionuclide[23], and $^{131}$I and $^{90}$Y are two most widely used radionuclides for radiotherapy[24,25]. High quality in vivo optical images can be quickly achieved (scan time, no more than 5-min) for all of these radionuclides in high sensitivity (administration dose in µCi range). These encouraging results suggest that the radioactive OI can be a powerful tool for fast and preliminary evaluation of $^{18}$F, $^{131}$I, and $^{90}$Y labeled compounds. This will be especially important for $^{90}$Y based agents development, since it has been very difficult to obtain in vivo information of a $^{90}$Y agent through non-invasive imaging method.

Compared to conventional fluorescence and bioluminescence imaging, radioactive OI has some unique properties. It has continued emission wavelength, therefore, a radioactive probe can be monitored at different wavelengths. More importantly, radioactive OI does not require excitation light, which is a significant advantage over traditional OI. The radioactive OI signal generated by radioactive probe is also always on, which is very different from fluorescence and bioluminescence probes. It should be noticed that although only $\beta^+$ and $\beta^-$ emitters were evaluated in this study, any radionuclides ($\alpha$, $\beta^+$, $\beta^-$, electron capture, etc.) which emit charged particles is likely suitable for radioactive OI. The detection and imaging sensitivity also depends on the physical properties of radionuclides. Certainly radioactive OI shares some common disadvantages as other OI techniques: poor tissue penetration and relatively poorer quantification ability compared with PET and SPECT. But regardless of these disadvantages, OI techniques have advanced rapidly over the past couple of years. OI has evolved from a basic research tool to a modality which has great potential in patient imaging. Future research in radioactive OI will likely further accelerate the translation of OI into clinical application.

Methods

Materials: Na$^{131}$I, Na$^{125}$I, $^{90}$YCl$_3$, and $^{111}$InCl$_3$ were purchased from Perkin Elmer (Waltham, Mass.). Sodium pertechnetate (Na$^{99m}$TcO$_4$) was obtained from GE Healthcare Nuclear Pharmacies (Sunnyvale, Calif.), $^{177}$LuCl$_3$ and $^{64}$CuCl$_2$ was provided by the University of Missouri Research Reactor (Columbia, Mo.) and the Department of Medical Physics, University of Wisconsin at Madison (Madison, Wis.), respectively. [$^{18}$F]FDG and Na$^{18}$F were produced by Radiochemistry Facility at Stanford University (Stanford, Calif.). Heterodimer peptide DOTA-RGD-BBN was provided by Dr. Xiaoyuan Chen as reported recently[18-20]. All other standard synthesis reagents were purchased from Sigma-Aldrich Chemical Co. (St. Louis, Mo.). Human prostate cancer cell line PC3 was obtained from American Type Culture Collection (Manassas, Va.). Rat glioma cell C6-fluc was from Dr. Gambhir's laboratory. Female athymic nude mice (nu/nu), obtained from Charles River Laboratories Inc. (Cambridge, Mass.) were at 4-6 weeks of age. All instruments including electrospray ionization mass spectrometry (ESI-MS), reverse phase high performance liquid chromatography (RP-HPLC), PET dose calibrator, and tumor cell lines are the same as described in our previous publication[26].

Tumor models: All animal studies were carried out in compliance with Federal and local institutional rules for the conduct of animal experimentation. C6-fluc cells were cultured in DMEM medium supplemented with 10% fetal bovine serum (FBS) and 1% penicillin-streptomycin (Invitrogen Life Technologies, Carlsbad, Calif.). PC3 cells were cultured in F-12K medium with 2 mM L-glutamine supplemented with 10% FBS and 1% penicillin-streptomycin in a sealed flask. All the cell lines were maintained in a humidified atmosphere of 5% CO$_2$ at 37° C., with the medium changed every other day. A confluent monolayer was detached with trypsin and dissociated into a single cell suspension for further cell culture. Approximately 1×10$^6$ C6-fluc or PC3 cells suspended in PBS were implanted subcutaneously in the flanks of nude mice. Tumors were allowed to grown to a size of 500 to 750 mg (2-3 weeks), and the tumor bearing mice were subjected to in vivo imaging and biodistribution and studies.

In vivo bioluminescence imaging: The mice bearing subcutaneous C6-fluc tumors were anesthetized in a chamber filled with 2% isofluorane in oxygen, and then transferred to the light-tight chamber of the IVIS Spectrum small animal imaging system (Caliper Life Sciences, Hopkinton, Mass.). D-Luciferin was injected intraperitoneally and the images were acquired at 10 min after injection.

Radioactive optical imaging: In vivo radioactive OI was also performed with an IVIS Spectrum system. Wavelength-resolved spectral imaging was carried out suing a 18 narrow bands emission filters set (490-850 nm). Animals were placed in a light-tight chamber under isofluorane anesthesia. Each acquisition, with or without filters, took 1-5 min for all studies. Images were acquired and analyzed using Living Image 3.0 software (Caliper life sciences, Hopkinton, Mass.). Quantification of Radioactive OI images was corrected in accordance with radionuclides' respective physical decay properties. Optical signal was normalized to photons per second per centimeter square per steradian (p/s/cm$^2$/sr). Identical setting was used for in vitro Radioactive OI. For in vivo imaging study, normal mice or mice bearing either C6-fluc or PC3 (n=3 for each imaging probe) were injected via tail vein with Na$^{18}$F (5.3-5.7 MBq, 140-150 µCi), [$^{18}$F]FDG (10.4-11.3 MBq, 280-305 µCi), Na$^{131}$I (2.2-2.3 MBq, 59-61 µCi), $^{90}$YCl$_3$ (1.8-2.0 MBq, 48-54 µCi) or $^{90}$Y-RGD-BBN (2.6-3.3 MBq, 70-90 µCi). For [$^{18}$F]FDG imaging study, the mice were fasted overnight prior to the experiment.

PET imaging: Small-animal microPET imaging of tumor-bearing mice was performed on a small-animal PET R4 rodent model scanner (Siemens Medical Solutions USA, Inc., Knoxville, Tenn.). A group of mice (n=3) bearing C6-fluc were injected with [$^{18}$F]FDG (10.4-11.3 MBq, 280-305 µCi) via tail vein. At 0.5, 1 and 2 h p.i., the mice were anesthetized with 2% isofluorane (Aerrane' Baxter, Deerfield, Ill.), and placed in the prone position and near the center of the filed of view (FOV) of small-animal PET scanner. A three-min static scans were obtained and the images were reconstructed by a two-dimensional ordered subsets expectation maximum (OSEM) algorithm. No background correction was performed. The method for quantification analysis of the images was the same as reported previously[27].

SPECT/CT imaging: Images were obtained on an Imtek microCAT II/SPECT system (Imtek, Inc. Knoxville, Tenn.) at 1 h after injection of 2.2-2.3 MBq $^{131}$I through tail vein. Computed tomography images were acquired immediately after the SPECT scan. Co-registration of CT and SPECT images was done using Amira software (Amira 3.1, Mercury Computer Systems GmbH, Berlin, Germany). No X-ray contrast agent was used in this study.

Statistical methods: Statistical analysis was performed using the Student's t-test for unpaired data. A 95% confidence level was chosen to determine the significance between groups, with $P<0.05$ being significantly different. References, each of which is incorporated herein by reference 1. Massoud, T. F. & Gambhir, S. S. Molecular imaging in living subjects: seeing fundamental biological processes in a new light. *Genes Dev.* 17, 545-590 (2003).
2. Gambhir, S. S. Molecular imaging of cancer with positron emission tomography. *Nat. Rev. Cancer* 2, 683-693 (2002).
3. Weissleder, R. Molecular imaging in cancer. *Science* 312, 1168-1171 (2006).
4. Weissleder, R. Scaling down imaging: molecular mapping of cancer in mice. *Nat. Rev. Cancer* 2, 11-18 (2002).
5. Nakel W (1994). The elementary process of bremsstrahlung. *Phys Rep* 243, 317-353.
6. Haug E & Nakel W (2004). The elementary process of bremsstrahlung. River Edge N.J.: World Scientific. p. *Scientific lecture notes in physics*, 73.
7. Shen S et al. (1994a) Planar gamma camera imaging and quantitation of yttrium-90 bremsstrahlung. *J Nucl Med* 35, 1381-1389.
8. Shen S et al. (1994b). Quantitative bremsstrahlung imaging of yttrium-90 using a Wiener filter. *Med Phys* 21, 1409-1417.
9. Siegel J A & Khan S H (1996). Body contour determination and validation for bremsstrahlung SPECT imaging. *J Nucl Med* 37, 495-497.
10. Siegel JA (1994). Quantitative bremsstrahlung SPECT imaging: attenuation-corrected activity determination. *J Nucl Med* 35, 1213-1216.
11. Ito S et al. (2009). $^{90}$Y bremsstrahlung emission computed tomography using gamma cameras. *Ann Nucl Med* 23, 257-267.
12. Minarik D et al. (2008). Evaluation of quantitative $^{90}$Y SPECT based on experimental phantom studies. *Phys Med Biol* 53, 5689-5703.
13. Quon, A. & Gambhir, S. S. FDG-PET and beyond: molecular breast cancer imaging. *J. Clin. Oncol.* 23, 1664-1673 (2005).
14. Iagaru, A. et al. Novel strategy for a cocktail 18F-fluoride and 18F-FDG PET/CT scan for evaluation of malignancy: results of the pilot-phase study. *J. Nucl. Med.* 50, 501-505 (2009).
15. Buscombe, J., Hirji, H. & Witney-Smith, C. Nuclear medicine in the management of thyroid disease. *Expert Rev. Anticancer Ther.* 8, 1425-1431 (2008).
16. Kogai, T., Taki, K. & Brent, G. A. Enhancement of sodium/iodide symporter expression in thyroid and breast cancer. *Endocr. Relat. Cancer.* 13, 797-826 (2006).
17. Chung, J. K. Sodium iodide symporter: its role in nuclear medicine. *J. Nucl. Med.* 43, 1188-200 (2002).
18. Liu, Z. et al. Small-animal PET of tumors with $^{64}$Cu-labeled RGD-bombesin heterodimer. *J. Nucl. Med.* 50, 1168-1177 (2009).
19. Liu, Z., Niu, G., Wang, F. & Chen, X. $^{68}$Ga-labeled NOTA-RGD-BBN peptide for dual integrin and GRPR-targeted tumor imaging. *Eur. J. Nucl. Med. Mol. Imaging.* 36, 1483-94 (2009).
20. Liu, Z., Yan, Y., Chin, F. T., Wang F. & Chen, X. Dual integrin and gastrin-releasing peptide receptor targeted tumor imaging using $^{18}$F-labeled PEGylated RGD-bombesin heterodimer $^{18}$F-FB-PEG3-Glu-RGD-BBN. *J. Med. Chem.* 52, 425-32 (2009).
21. Breeman W A, et al. Reduction of skeletal accumulation of radioactivity by co-injection of DTPA in [$^{90}$Y-DOTA$^0$, Tyr$^3$]octreotide solutions containing free $^{90}$Y$^{3+}$. *Nucl. Med. Biol.* 31, 821-824 (2004).
22. Sevick-Muraca E M, et al. Imaging of lymph flow in breast cancer patients after microdose administration of a near-infrared fluorophore: feasibility study. *Radiology.* 246, 734-741 (2008).
23. Okarvi, S. M. Recent progress in fluorine-18 labelled peptide radiopharmaceuticals. *Eur. J. Nucl. Med.* 28, 929-938 (2001).
24. Oriuchi, N., Higuchi, T., Hanaoka, H., Iida, Y. & Endo, K. Current status of cancer therapy with radiolabeled monoclonal antibody. *Ann. Nucl. Med.* 19, 355-65 (2005).
25. van Essen, M., et al. Peptide-receptor radionuclide therapy for endocrine tumors. *Nat. Rev. Endocrinol.* 5, 382-93 (2009).
26. Cheng, Z., et al. Small-animal PET imaging of human epidermal growth factor receptor type 2 expression with site-specific $^{18}$F-labeled protein scaffold molecules. *J Nucl Med.* 49, 804-813 (2008).

Example 2

Molecular imaging combines molecular biology and medical imaging and allows the visualization of cellular processes in living subjects at the molecular level. Reporter gene/reporter probe technology is a powerful molecular imaging technique which provides a generalizable method for non-invasive imaging of protein expression, protein function and protein-protein interaction (1). Reporter gene imaging has been widely used in biomedical research to address many fundamental biological problems, including monitoring the progress of cancers, screening drugs, monitoring gene therapy and tracking the fate of cells (2).

Many reporter gene/reporter probe systems have been coupled with different imaging modalities over the past two decades. For reporter gene optical bioluminescence imaging (BLI), luciferase as a reporter gene with D-luciferin or coelenterazine as the substrate, has been widely used (2). Because of the extremely low background, this imaging system can monitor luminescence light with high sensitivity. However the light produced from the enzyme/substrate reaction usually has a peak less than 600 nm and thus displays poor tissue penetration (3). For nuclear imaging, a well-established radionuclide-based imaging reporter gene/reporter probe system is the herpes simplex virus type 1 thymidine kinase (HSV1-tk) enzyme and radiolabeled uracil nucleoside or acycloguanosine derivatives such as 9-(4-[$^{18}$F]-fluoro-3-[hydroxymethyl]butyl)guanine ([$^{18}$F]FHBG) or 2'-[$^{18}$F]-fluoro-5-ethyl-1-β-D-arabinofuranosyluracil ([$^{18}$F]FEAU) as the reporter probe (4-5). Another is the sodium iodide symporter and the reporter probe radioiodine or $^{99m}$Tc-pertechnetate (6-7). In using these approaches, several disadvantages arise, namely that nuclear reporter gene systems require positron emission tomography (PET) or single photon emission computed tomography (SPECT) which are expensive and may not be easily accessible to many researchers.

Recently, we and others have found that a variety of radioactive materials (β$^{+}$ and β$^{-}$ emitters) could be detected by OI techniques. It has been successfully demonstrated that radioactive molecular probes such as 2-deoxy-2-[$^{18}$F]fluoro-D-glucose ([$^{18}$F]FDG), Na$^{18}$F, Na$^{131}$I, $^{90}$YCl$_3$ and $^{90}$Y labeled tumor targeting peptides could be non-invasively imaged in small animals by optical imaging instruments. This is mainly attributed to the ability of radioactive materials to produce low energy visible photons (1.2-3.1 eV, 400-1000 nm) associated with Cerenkov or Bremsstrahlung radiation (8-11). In this research study, we further evaluated the feasibility of using OI to monitor the nuclear reporter gene/reporter probe systems. HSV1-tk and [$^{18}$F]FHBG was thus chosen as a model system in this study. The C6 rat glioma cell line stably transfected with HSV-sr39tk plasmids (C6-tk) (12) was used, and the in vitro [$^{18}$F]FHBG uptakes in C6-tk cells were measured by both an IVIS optical imaging system (Caliper) and a gamma counter (Perkin Elmer). Finally, we performed in vivo imaging studies of the reporter gene/reporter probe using both OI and PET followed by a biodistribution study.

The in vitro [$^{18}$F]FHBG cell uptake study was performed as previously described with minor modifications (12). Briefly, C6-tk cells were seeded into 12-well plates at a density of 5×10$^5$ cells per well 12 h prior to the experiment. The C6 cell line without transfection was used as a negative control. The cells were then incubated with [$^{18}$F]FHBG (~10$^7$ kBq/well, 3 µCi/well) at 37° C. for 15, 30, 60 and 120 min. Tumor cells were washed 3 times with chilled phosphate buffered saline (PBS) and harvested with 0.25% trypsin/0.02% ethylenediaminetetraacetic acid (EDTA) (Invitrogen). The cell suspensions were transferred to a 96-well flat bottom black plate (Nunc) and imaged by an IVIS 200 system (Caliper). Luminescent images were taken without a filter [see FIG. 2.1(a)]. The exposure time was 5 min. Then the radioactivity of the cell suspension was measured in a gamma counter (Packard, Meriden, Conn.). The in vitro cell uptake results were expressed as the percentage of the applied activity with decay correction [see FIG. 2.1(b)]. Experiments were performed twice with triplicate samples for each time point. Both OI and gamma counting show a rapid and high uptake of [$^{18}$F]FHBG in C6-tk cells, whereas non transfected C6 cells show very low cell uptake [see FIG. 2.1(a) and 2.1(b)]. More importantly, an excellent correlation has been obtained between OI and gamma counting results [see FIG. 2.1(c), r$^2$>0.95]. These findings lay the foundation for further in vivo studies to validate the feasibility of using OI for monitoring the nuclear reporter gene system.

Prior to in vivo imaging, comparison studies were performed to evaluate the detection sensitivity of IVIS 200 OI system (Caliper) and small animal PET (microPET R4 rodent model scanner, Siemens Medical Solutions USA, Inc.). Serial samples containing different amount of radioactivity (Na$^{18}$F) were prepared in 300 µl of water (ranged from 0.01-1 µCi) and imaged by OI and PET [see FIG. 2.1(d)]. A 5 min imaging time was applied to both modalities. For PET, signal-to-noise (S/N) ratio of 32.1 is obtained from 0.01 µCi (0.44 kBq) of $^{18}$F, while OI can detect 0.1 µCi (4.4 kBq) of $^{18}$F with a S/N ratio of 1.7. It was found that $^{18}$F samples lower than 0.1 µCi could hardly be differentiated from background in OI images. PET excels OI in both sensitivity and imaging contrast. The different sensitivity between the two modalities could be attributed to the weak photon production of radionuclides and thus low signal intensities from $^{18}$F in OI. Although less sensitive than PET, OI demonstrates promising detection capability and warrants further in vivo experiments.

All animal studies were carried out in compliance with federal and local institutional rules for the conduct of animal experimentation. Mice bearing two tumors (C6-tk and C6) were then used for in vivo studies. The C6-tk (left) and C6 (right) cells were injected contra-laterally in the dorsal shoulder region of each mouse (2×10$^6$ cells/mouse; athymic nude mice were purchased from Charles River Laboratories, n=6). Approximately 10 days later, when tumor size reached about 1-1.5 cm in diameter, small animal PET and OI were performed using the mice and the PET probe [$^{18}$F]FHBG. Images at 1 h and 2 h were obtained by both OI and PET. Results are shown by average radiance (photon/second/cm$^2$/str) for OI and percentage of injected dose per gram (% ID/g) for PET based on the method previously described (13). At 1 h after tail vein injection of [$^{18}$F]FHBG (10-11 MBq, 270-300 µCi), C6-tk tumors can be clearly delineated using OI while there is minimum tracer uptakes in the control C6 tumors (see FIG. 2.2). The strong signals in the lower part of the mouse body [FIG. 2.2 (a)] are due to the presence of the radioactivity in the bladder. PET imaging shows a similar pattern of tracer distribution [FIG. 2.2 (b)]. At 2 h post-injection, with the elimination of [$^{18}$F]FHBG, only C6-tk tumors can be clearly visualized in both imaging modalities (see FIG. 2.2). FIG. 2.2 (c) shows the statistical analysis of tumor to normal tissue (T/N) ratio for both imaging modalities at 1 h and 2 h post-injection. Compared to OI, PET displays higher T/N ratios (OI: 2.6±0.5 at 1 h, 5.1±1.1 at 2 h; PET: 43.2±8.4 at 1 h, 143.0±14.8 at 2 h).

To further compare the imaging results obtained from OI and PET, biodistribution studies were conducted. Mice were sacrificed and different organs were collected at 1 h post-injection of [$^{18}$F]FHBG. OI images were obtained for these radioactive organs and quantification analysis of optical images was performed using Living Image software version 3.1 [see FIG. 2.3(a)]. Meanwhile, the radioactivity of the organs was also measured using a gamma counter after weighing, and the radioactivity uptake in the tumor and normal tissues was calculated and expressed as a percentage of the injected radioactive dose per gram of tissue (% ID/g) [see FIG. 2.3(b)]. For optical imaging of the organs, the C6-tk tumor, the kidney, and the intestine were clearly visible at 1 h post-injection. Quantification analysis also revealed that they were the organs with the highest optical signals, while all the other organs displayed minimum light intensities [see FIG. 2.3(a)]. It was also found that biodistribution patterns obtained through these two approaches were consistent [see FIG. 2.3(a) and 2.3(b)]. Compared with the intestines, much higher signals from the kidney are observed, which indicates that the clearance route of [$^{18}$F] FHBG is mainly through urinary excretion.

The ratio of kidney to tumor uptake of [$^{18}$F]FHBG at 1 h was also calculated to be 2.3 vs. 1.4, for gamma counting vs. OI quantification, respectively. This discrepancy could mainly originate from the diverse optical properties of different tissues, which ultimately affects light imaging and quantification. Compared with the C6-tk tumor, the kidney contains more hemoglobin that absorbs more optical photons. Moreover, unlike high energy gamma rays, the low energy photons have very weak tissue penetrability. Light sources deeper in the tissue contribute less for the total optical signals than those closer to the surface. Therefore the kidney/tumor ratio measured by OI is lower than that obtained by gamma counting. Overall, PET has a better quantitative capability than OI. However, radioactive OI can still serve as a qualitative or semiquantitative research tool for radioactive reporter probe studies. The radioactive OI signals also have a uniquely wide wavelength of emission spectrum (9). The emissions in the near infra-red range are especially favorable for OI in living subjects. In comparison with current reporter gene imaging using BLI probes, radioactive reporter probes may offer a better option for 3D OI reconstruction.

In conclusion, the low energy photons produced by [$^{18}$F] FHBG radiation can be easily imaged by OI instruments both in vitro and in living small animals. This work for the first time demonstrates the feasibility of using OI as an alternative tool for monitoring reporter gene expression with radioactive probes. Considering the wide availability of OI instruments and many radioactive reporter probes such as [$^{18}$F]FHBG and radioiodine, OI with radioactive reporter probes will facilitate and broaden the applications of reporter gene/reporter probe techniques in medical research. References, each of which is incorporated herein by reference 1. J. J. Min and S. S. Gambhir, "Molecular imaging of PET reporter gene expression," Handb Exp Pharmacol 185 Pt 2), 277-303 (2008)
2. T. F. Massoud and S. S. Gambhir, "Molecular imaging in living subjects: seeing fundamental biological processes in a new light," Genes Dev 17(5), 545-580 (2003)
3. J. W. Hastings, "Chemistries and colors of bioluminescent reactions: a review," Gene 173(1 Spec No), 5-11 (1996)
4. J. G. Tjuvajev, A. Joshi, J. Callegari, L. Lindsley, R. Joshi, J. Balatoni, R. Finn, S. M. Larson, M. Sadelain and R. G. Blasberg, "A general approach to the non-invasive imaging of transgenes using cis-linked herpes simplex virus thymidine kinase," Neoplasia 1(4), 315-320 (1999)
5. S. S. Gambhir, J. R. Barrio, M. E. Phelps, M. Iyer, M. Namavari, N. Satyamurthy, L. Wu, L. A. Green, E. Bauer, D. C. MacLaren, K. Nguyen, A. J. Berk, S. R. Chemy and H. R. Herschman, "Imaging adenoviral-directed reporter gene expression in living animals with positron emission tomography," Proc Natl Acad Sci USA 96(5), 2333-2338 (1999)
6. T. Groot-Wassink, E. O. Aboagye, M. Glaser, N. R. Lemoine and G. Vassaux, "Adenovirus biodistribution and noninvasive imaging of gene expression in vivo by positron emission tomography using human sodium/iodide symporter as reporter gene," Hum. Gene Ther. 13(14), 1723-1735 (2002)
7. A. Merron, I. Peerlinck, P. Martin-Duque, J. Burnet, M. Quintanilla, S. Mather, M. Hingorani, K. Harrington, R. Iggo and G. Vassaux, "SPECT/CT imaging of oncolytic adenovirus propagation in tumours in vivo using the Na/I symporter as a reporter gene," Gene Ther. 14(24), 1731-1738 (2007)
8. R. Robertson, M. S. Germanos, C. Li, G. S. Mitchell, S. R. Chemy and M. D. Silva, "Optical imaging of Cerenkov light generation from positron-emitting radiotracers," Phys Med Biol 54(16), N355-365 (2009)
9. H. Liu, G. Ren, Z. Miao, X. Zhang, X. Tang, P. Han, S. S. Gambhir and Z. Cheng, "Molecular Optical Imaging with Radioactive Probes," PLoS ONE 5(3), e9470 (2010)
10. A. E. Spinelli, D. D'Ambrosio, L. Calderan, M. Marengo, A. Sbarbati and F. Boschi, "Cerenkov radiation allows in vivo optical imaging of positron emitting radiotracers," Phys Med Biol 55(2), 483-495 (2010)
11. A. Ruggiero, J. P. Holland, J. S. Lewis and J. Grimm, "Cerenkov Luminescence Imaging of Medical Isotopes," J Nucl Med 51(7), 1123-1130 (2010)
12. S. S. Gambhir, E. Bauer, M. E. Black, Q. Liang, M. S. Kokoris, J. R. Barrio, M. Iyer, M. Namavari, M. E. Phelps and H. R. Herschman, "A mutant herpes simplex virus type 1 thymidine kinase reporter gene shows improved sensitivity for imaging reporter gene expression with positron emission tomography," Proc Natl Acad Sci USA 97(6), 2785-2790 (2000)
13. Z. Cheng, O. P. De Jesus, M. Namavari, A. De, J. Levi, J. M. Webster, R. Zhang, B. Lee, F. A. Syud and S. S. Gambhir, "Small-animal PET imaging of human epidermal growth factor receptor type 2 expression with site-specific 18F-labeled protein scaffold molecules," J Nucl Med 49(5), 804-813 (2008)

Example 3

In recent years molecular imaging has become a standard of care in diagnosing, staging, and monitoring the treatment of cancer, as well as neurological and cardiovascular diseases [1-3]. In contrast to traditional diagnostic imaging modalities such as computed tomography (CT) and ultrasound, which provide predominantly anatomical information, molecular imaging offers unique information about the underlying biochemistry with molecular specificity. Optical imaging, magnetic resonance imaging (MRI), and positron emission tomography (PET) are mainly used for non-invasive molecular imaging. While MRI has limited sensitivity (contrast agent concentration: $10^{-3}$ to $10^{-5}$ mol/L), both optical imaging and PET provide high sensitivity (probe concentration: $10^{-11}$ to $10^{-12}$ mol/L). Advantages of optical imaging include rapid image acquisition, low cost, and the absence of ionizing radiation. However, it suffers from limited depth penetration due to the strong attenuation of light by biological tissue. Alternatively, optical endoscopes and laparoscopes are used to deliver light directly to the internal organs through natural or surgical orifices. While in conventional white light endoscopy diffusely reflected light from the tissue surface is imaged to visualize lesions or structural changes, several new optical endoscopy technologies exploit light properties such as optical coherence and fluorescence [4,5]. For example, fluorescence emitted from both endogenous molecules (such as aromatic amino acids, NADH (nicotinamide adenine dinucleotide) and FAD (flavin adenine dinucleotide)) and exogenous fluorescent labeled probes are used to determine the biochemical and molecular changes in diseased tissues [6,7]. These unparalleled abilities made optical endoscopy a powerful minimally invasive tool in diagnosing and treating a wide spectrum of human diseases. However, it still remains a challenge to translate optical molecular contrast agents from bench side (e.g., small animal imaging studies) to clinical applications. This is evident from the fact that only three optical contrast agents, indocyanine green (ICG), methylene blue, and fluorescein have been approved by the US Food and Drug Administration (FDA) for use in patients for non-targeted imaging such as improving the contrast/visibility of tissue structure or the blood vasculature.

On the other hand, many radioactive probes/tracers have been approved by the FDA for PET or SPECT and are injected. These radioactive probes target intracellular, cell surface, or extracellular matrix molecules that are overexpressed in different diseases. For example, $^{18}$F-FDG is used in conjunction with PET to assess glucose metabolism in the heart, lungs, the brain and several types of malignant tumors [1 8-9]. $^{18}$F-FDG-PET is therefore used for diagnosis, staging, and monitoring treatment of different cancer types such as lung cancer, breast cancer, colorectal cancer, melanoma, Hodgkin's disease and non-Hodgkin's lymphoma. It has also been approved for use in diagnosing Alzheimer's disease. Similarly, several $^{18}$F labeled metabolic tracers (e.g., $^{18}$F-Choline) and non-metabolic tracers such as $^{18}$F labeled Arginine-Glycine-Asparatic Acid (RGD) peptide that targets cell adhesion receptor integrin $\alpha_v\beta_3$, $^{18}$F-FAZA and $^{18}$F-FM ISO (tracers that selectively accumulate in hypoxic cells), anti-$^{18}$F-FACBC (an amino acid analogue) are in pilot clinical trials [10-16]. A dedicated PET-CT scanner is used to precisely combine the spatial distribution of metabolic or biochemical activity obtained from these PET probes with anatomical information obtained by CT for non-invasive molecular imaging. The current limitations of PET, however, include limited spatial resolution (several mm), relatively high cost, time consuming, and limited use in endoscopy mode. These issues limit applications of PET probes in interventional molecular imaging procedures such as different endoscopy procedures, robotic surgeries including tumor resection (ex: robotic prostatectomy), lymph node biopsy, and in certain cardiovascular applications.

New advancements in optical molecular imaging are moving beyond conventional fluorescence imaging. In the last couple of years, Cerenkov luminescence imaging (CLI) has emerged as an active field of research in biomedical community [17-20], since it offers the potential of cost-effective molecular imaging that combines the above-mentioned advantages of both nuclear medicine and optical imaging. Cerenkov light is originated when charged nuclear particles such as $\beta^+$ (positron) or $\beta^-$ (nuclear electron), emitted from radionuclides, travel at superluminal velocity in any dielectric medium such as biological tissue or water. Therefore CLI can be performed with positron emitters, unlike SPECT that uses gamma ($\gamma$) rays and PET that uses positrons. Cerenkov radiation is continuous and occurs mainly in the visible (more intense in the blue) region of the electromagnetic spectrum in the wavelength range of 400-1000 nm. This facilitates in vivo optical imaging of living subjects intravenously administered with a wide variety of above mentioned radioactive probes that specifically target tumors, using commercially available optical imaging systems (e.g., IVIS 200 Spectrum, Caliper Life Sciences) that are equipped with cooled CCD cameras. Like conventional optical imaging, one of the main challenges of CLI is the limited depth of penetration due to strong scattering of Cerenkov light as it propagates through biological tissue. This limits application of CLI to potentially image superficial tumors such as melanoma. In order to extend its applications in endoscopy (e.g., esophageal and bladder cancer), it is highly desirable that optical signals from radionuclides can be imaged using conventional endoscopes and fiber optic light guides. Since the origin and source of the signal are the same in both PET and CLI, the combined PET and Cerenkov endoscopy-guided tumor resection can lead to a more accurate method of diagnosing and treating the tumor using the same probe. We recently showed feasibility of intraoperative imaging of optical signals from radionuclides for identifying tumors in mice models using our custom made fiber optic system (21).

In this Example, we further demonstrate that optical signals from radionuclides can be efficiently guided through conventional optical fibers/clinical endoscopes and can be detected with a sensitive CCD camera. We study limits of detecting optical signals emitted from phantom samples containing different concentrations of $^{18}$F-FDG using different optical fibers and endoscopes. We further validate feasibility of detecting optical signals emitted from C6 glioma tumor bearing mice, intravenously administered with $^{18}$F-FDG, using an endoscopy imaging system that includes an optical fiber coupled to a CCD camera. Since PET probes have the capability to targeting cancer cells in different regions of the body, the optical signals emitted from these cells can then be detected using conventional endoscopes routinely used in the clinic. CLI using a conventional endoscope or a fiber optic light guide can therefore be of help in surgical oncology in delineating tumor margins.

Methods and Materials:
Experimental Setup:

Typical optical endoscopy imaging system includes an endoscope (usually made out of optical fibers and/or optical lenses such as grin/rod lenses), a white light source, and a CCD camera that is connected to the computer monitor. We demonstrate feasibility of Cerenkov luminescence endoscopy (CLE) using an IVIS imaging system 200 series (Caliper Life Sciences) as it includes a sensitive low noise CCD camera (Quantum efficiency >85% in 500-700 nm, read noise <5 electrons RMS (root mean square), dark current <100 electrons/s/cm$^2$, minimum detectable radiance <70 photons/s/sr/cm$^2$, operating temperature −105° C., field of view 3.9×3.9 cm to 26×26 cm (3.9, 6.5, 13, 19.5, 26 cm)) that is necessary to visualize weak optical signals emitted from trace levels of radioactive molecules. As shown in FIG. 3.1, we modified the IVIS imaging system 200 series to image phantom samples/animal subjects (denoted by "S"), administered with radioactive samples, using different optical fibers/endoscopes (OF). The subject "S" was placed outside the field of view (FOV) of the imaging system. The input end of the OF was placed close to the subject "S". The output end of the "OF" faced the CCD camera such that the image transmitted by the output end was imaged on to the CCD camera using a relay lens system. The optical signal was normalized to photons per second per centimeter square per steradian (p/s/cm$^2$/sr). Identical settings were used for both in vitro and living mouse experiments.

Endoscopes and Optical Fibers:

Various diagnostic instruments used in medical examination fall within the broad definition of remote sensing, although the target tissue being analyzed is close to the sensor, which may be exterior to the body, placed on the body's surface, or inserted inside the body to examine internal organs. Most of these instruments work in active modes by sending either EM radiation (such as visible and RF radiation) or acoustic waves into the body and then sensing/imaging respective reflected signals. In this work we used conventional endoscopes and fiber optic cables/bundles in a passive mode for remote sensing/imaging of optical signals from radionuclides emitted from a PET probe, $^{18}$F-FDG. In a conventional optical endoscope the distal tip contains the optics required for illuminating and collecting endoscopic images, channels for air, water and other instrument delivery. The proximal end of the endoscope contains several control knobs and switches for bending (as high as 270 degrees) the distal end and controlling the instrument channels. While the distal end of the endoscope was placed close to the tissue under investigation, the proximal end that transmits the image was imaged on to the CCD camera using a lens system. The optical signals propagating through the tissue was isotropically scattered and only a fraction of this light is collected by the endoscope. High optical throughput or etendue is therefore critical for high sensitivity measurement such as detecting weak light through optically scattering medium (e.g., biological tissue). The maximum angle at which an endoscope can collect the light can be as high as 70 degrees. As shown in FIG. 3.2, the etendue of a typical optical fiber is proportional to the area of the fiber core and square of numerical aperture (NA) of the fiber. A high NA allows light to propagate down the fiber in rays both close to the axis and at various angles, allowing efficient coupling of light into the fiber. Etendue therefore, is a limiting function of system throughput. In the next section, we employed several optical endoscopes and conventional optical fibers with different etendues to study the limits of detection of optical light from $^{18}$F-FDG solution in vitro.

$^{18}$F-FDG Protocol/Tumor Model $^{18}$F-FDG was produced by the Radiochemistry Facility at Stanford University using standard procedures. Rat glioma cell line C6 was obtained from American Type Culture Collection (Manassas, Va.). Female athymic nude mice (nu/nu), obtained from Charles River Laboratories, Inc (Cambridge, Mass.) were at 4-6 weeks of age. A CRC-15R PET dose calibrator (Capintec Inc., Ramseb, N.J.) was used for all radioactivity measurements. All animal studies were carried out in compliance with federal and local institutional rules for the conduct of animal experimentation. C6 cells were cultured in DMEM medium supplemented with 10% fetal bovine serum (FBS) and 1% pencillin/streptomycin (Invitrogen Life Technologies, Carlsbad, Calif.). The cell line was maintained in a humidified atmosphere of 5% $CO_2$ at 37° C., with the medium changed every other day. A 75% confluent monolayer was detached with trypsin and dissociated into a single cell suspension for further cell culture. Approximately 1×10$^6$ C6 cells suspended in phosphate buffered saline (PBS, 0.1 M, pH=7.2, Invitrogen, Carlsbad, Calif.) were implanted subcutaneously in the leg of nude mice. Tumors were allowed to grow to a size of 150 to 200 mm$^3$ over 2-3 weeks, and the tumor bearing mice were subjected to in vivo imaging studies. For all in vivo and in vitro studies, radioactive PET probes were diluted in PBS. As shown in FIG. 3.1, animals (denoted by "S") were placed in a light-tight chamber under isoflurane anesthesia. For the $^{18}$F-FDG imaging study, the mice were fasted overnight prior to the experiment and kept anesthetized during the experiment. For the in vivo imaging study, normal mice or mice bearing C6 glioma tumor were injected with $^{18}$F-FDG (0.9 mCi) via tail vein.

Results and Discussion

First we performed series of studies to quantify the contribution of optical signals from radionuclides and scintillation occurring when high energy gamma radiation is irradiating the 6 mm optical fiber optic bundle using both $^{64}$CuCl$_2$ and $^{18}$F-FDG radioactive solutions. These studies include blocking the coupling of optical signals into the fiber using a thick black paper (to record gamma scintillation), unblocking by removing the black paper (to record all luminescence), and also removing the radioactive samples (to measure the background). Our experimental results show that the contribution of gamma scintillation when the radioactive sample is within the field of view of the imaging system and when not in the field of view of the imaging system is about 9.5% and 3% respectively.

FIGS. 3.3(a-d) show optical signals from radionuclides from a phantom sample containing 10 µCi of $^{18}$F-FDG in 200 µL of PBS using different cystoscopes and optical fibers with a one minute exposure time. We used five different types of optical instruments in this study; clinical grade flexible and rigid cystoscopes (Karl Storz and Circom Acmi respectively), fiber optic bundle with a 6 mm active diameter, two conventional optical fibers with core diameters of 400 µm and 62.5 µm respectively. These instruments, denoted by "OF" (optical fiber) in FIG. 3.2, were placed in a modified IVIS imaging system. In FIG. 3.3(a), "S" represents the IVIS image of optical signals emitted from the 10 µCi $^{18}$F-FDG phantom sample. This image shows amount of light that is coupled into the distal end (marked by arrow) of all instruments in FIGS. 3.3(a-d). The optical signals rays that fall within the acceptance angle of the respective instruments are guided by total internal reflection and exit at the proximal end. The proximal ends of these instruments that transmit the Cerenkov signal were imaged, as shown in the right panel of FIGS. 3.3(a-d), by the CCD camera of the IVIS imaging system using a system of relay lenses. These images show that etendue/throughput of a 6 mm fiber optic bundle is relatively high compared to other instruments used in the study. We further investigated limits of detection of optical signals emitted from phantom samples containing decreasing concentrations of $^{18}$F-FDG using above mentioned cystoscopes and fibers. These results, plotted in FIG. 3.4, show that optical signals from as low as 1 µCi of $^{18}$F-FDG can be reliably detected using the above instruments. At any given concentration the signal detected by a 6 mm fiber optic bundle is higher compared to other instruments. All clinical endoscopes have a 6 mm accessory port to deliver special instruments/catheters into the body. This allows a 6 mm fiber optic bundle to pass through the port and reach the organ of interest in the body.

For $^{18}$F-FDG PET studies on a primary bladder tumor in humans a standard uptake value (SUV) of ~4.5 is reported [22]. Thus about 1 µCi of the probe is expected in 0.1 cc bladder cancer at 2 hours after intravenous injection of 10 mCi $^{18}$F-FDG (no decay correction). Although a 6 mm fiber optic bundle used in this study met this requirement, a more sensitive imaging system using specialty fibers that have high light transmission efficiency in the visible region can likely further improve the sensitivity and signal to noise ratio of the imaging system. Improved sensitivity can also be achieved using a radionuclide with a high mean energy beta particle [20].

We further validated our imaging system using in vivo small animal experiments following the protocol mentioned in the methods section. As shown in FIG. 3.2, the sample S that is outside the FOV of the imaging system was replaced with a mouse under anesthesia while using a OF that was a 6 mm fiber optic bundle. Mice (n=4) bearing subcutaneous C6 glioma were administered with 900 μCi of $^{18}$F-FDG via tail vein injection and imaged 90 minutes post-injection using the fiber bundle. This imaging time point was selected based on a previous study that shows tumor uptake of $^{18}$F-FDG increased significantly (P<0.05) over time (from 0.5-2 h) [20]. The distal end of the fiber bundle was placed (outside the body) close to several tissues of interest. The proximal end that transmits optical signals originated from the respective tissue (due to the $^{18}$F-FDG uptake) was imaged by the CCD camera of the imaging system. FIG. 3.5 shows Cerenkov luminescence imaging results from a 6 mm fiber bundle overlaid on a bright-field image of the mouse for anatomical reference. Relatively high signals from the subcutaneous tumor and brain indicate high tracer uptake in these organs.

To further characterize the distribution of $^{18}$F-FDG, tumors and other organs were removed from the sacrificed mice (n=4) and subjected to fiber optic imaging as mentioned above. Inset figure on top right corner of each organ in FIG. 3.6(a) represents average Cerenkov radiance detected by a 6 mm fiber optic bundle. FIG. 3.6(b) represents biodistribution of $^{18}$F-FDG in various tissues at one hour post injection in mice as measured using optical signals from radionuclides. Respective tissue optical signals was measured by a 6 mm fiber optic bundle (n=4 for all organs). Bars represent the average tissue uptake plus/minus standard deviation (expressed as % injected dose/g of tissue). High signal was mainly observed from the tumor, heart, brain, and kidney tissue samples.

Several technological revolutions taking place in fiber optics [23] and CCD/CMOS sensors can further improve the sensitivity of the imaging system in the near future. For example, a new type of crystal known as photonic crystals led to the development of a photonic crystal fiber (PCF). These fibers include a hexagonal bundle of hollow microtubes embedded in silica with in the center the fiber of photonic crystal. A PCF guides light by means of diffraction from a periodic structure, rather than total internal reflection used in this study. They have higher throughput as compared to conventional fibers. These developments will help translate CLI, using optimized optical endoscopes, into human studies such as robotic prostectomy. During robotic prostatectomy high resolution cameras and micro surgical instruments are remotely controlled to perform surgery safely without damaging delicate plexus of nerves (that are important to retain bladder control and sexual function) around the prostate gland. Remote sensing or imaging of Cerenkov light using optical endoscopy can therefore be useful in robotic surgeries, without the physician being exposed to potential radioactivity emitting from the radioactive tracers, for safely and precisely removing the tumor.

CONCLUSION

We demonstrate that optical signals can be efficiently coupled and transmitted through different clinical endoscopes and conventional optical fibers for eventual applications in clinical endoscopy. Our results show that coupling and transmission efficiency increases with an increase in the etendue of the endoscope/optical fiber. Optical signals from as low as 1 μCi of radioactivity emitted from $^{18}$F-FDG was reliably detected using a 6 mm fiber optic bundle. The feasibility of Cerenkov luminescence endoscopy using a 6 mm fiber was demonstrated by non-invasive in vivo imaging of mice bearing C6 glioma that were intravenously administered with $^{18}$F-FDG. Optical signals emitted from the tumor and other organs of the mouse, due to the $^{18}$F-FDG uptake, was non-invasively imaged using the endoscope at one hour post-injection. These results show higher tumor uptake of $^{18}$F-FDG compared to the surrounding tissue. We further validated our in-vivo results with respective ex-vivo imaging of different organs. In summary, this study demonstrates that Cherenkov luminescence endoscopy can likely be a useful tool in molecular imaging.

References, each of which is incorporated herein by reference

1. James, M. L.; Gambhir, S. S. A Molecular Imaging Primer: Modalities, Imaging Agents, and Applications. *Physiol Rev.* 2012 (In Press).
2. Weissleder R., "Scaling down imaging: molecular mapping of cancer in mice", *Nat Rev Cancer* 2: 11-18, 2002.
3. Massoud T. F, Gambhir S. S., "Molecular imaging in living subjects: seeing fundamental biological processes in a new light", *Genes Dev* 17: 545-580, 2003.
4. Tearney G. J., Waxman S., Shishkov M. S., Vakoc B. J., Suter M, Freilich M. I., Desjardins A. E., Oh W. Y., Bartlett L. A., Rosenberg M., Bouma B. E., "Three-dimensional coronary artery microscopy by intracoronary optical frequency domain imaging: First-in-man experience", *Journal of the American College of Cardiology: Imaging,* 1:752-61, 2008.
5. Wang, T. D., Crawford, J. M., Feld M. S., Wang Y., Itzkan, I., and Van Dam J., "In vivo identification of colonic dysplasia using fluorescence endoscopic imaging", *Gastrointest. Endosc.,* 49, 447-455, 1999.
6. Wu K., Liu J. J., Adams W., Sonn G. A., Mach K. E., Pan Y., Beck A. H., Jensen K. C., Liao J. C., "Dynamic real-time microscopy of the urinary tract using confocal laser endomicroscopy" *Urology,* 78 (1):225-31, 2011.
7. Kang D., Suter M. J., Boudoux C., Yoo H., Yachimski P. S., Puricelli W. P., Nishioka N. S., MinoKenudson M., Lauwers G. Y., Bouma B. E., Tearney G. J., "Comprehensive imaging of gastroesophageal biopsy samples by spectrally encoded confocal microscopy", *Gastrointestinal Endoscopy,* 71, 35-43, 2010.
8. Quon A., Gambhir S. S., "FDG-PET and beyond: molecular breast cancer imaging", *J. Clin, Oncol.,* 23:1664-1673, 2005.
9. Iagaru A., Mittra E., Yaghoubi S. S., Dick D. W., Quon A., et al., "Novel strategy for a cocktail 18F-fluoride and 18F-FDG PET/CT scan for evaluation of malignancy: results of the pilot-phase study", *J. Nucl. Med.,* 50; 501-505, 2009.
10. Schöder H., Larson S. M., "Positron emission tomography for prostate, bladder, and renal cancer", *Semin. Nucl. Med.,* 34:274-92, 2004.
11. Vees H., Buchegger F., Albrecht S., Khan H., Husarik D., Zaidi H., Soloviev D., Hany T. F., Miralbell R., "18F-choline and/or 11C-acetate positron emission tomography: detection of residual or progressive subclinical disease at very low prostate-specific antigen values (<1 ng/mL) after radical prostatectomy", *BJU Int.,* 99:1415-20, 2007.
12. Souvatzoglou M., Grosu A. L., Röper B., Krause B. J., Beck R., Reischl G., Picchio M., Machulla H. J., Wester H. J., Piert M., "Tumour hypoxia imaging with [18F] FAZA PET in head and neck cancer patients: a pilot study", *Eur J Nucl Med Mol Imaging,* 34:1566-75, 2007.
13. Bruehlmeier M., Roelcke U., Schubiger P. A., Ametamey S. M., "Assessment of hypoxia and perfusion in human brain tumors using PET with 18F-fluoromisonidazole and 15O-H2O", *J. Nucl. Med.,* 45:1851-9, 2004.

14. Amzat R., Taleghani P., Savir-Baruch B., Nieh P. T., Master V. A., Halkar R. K., Lewis M. M., Faurot M., Bellamy L. M., Goodman M. M., Schuster D. M., "Unusual presentations of metastatic prostate carcinoma as detected by anti-3 F-18 FACBC PET/CT", *Clin. Nucl. Med.*, 36:800-2, 2011.

15. Zhu A., Shim H., "Current molecular imaging positron emitting radiotracers in oncology", *Nucl. Med. Mol. Imaging.*, 45:1-14, 2011.

16. Buscombe J., Hirji H., Witney-Smith C., "Nuclear medicine in the management of thyroid disease", *Expert. Rev, Anticancer, Ther.*, 8: 1425-1431. 2008.

17. Robertson R., Germanos M. S., Li C., Mitchell G. S., Chemy S. R., et al. "Optical imaging of Cerenkov light generation from positron-emitting radiotracers", *Phys Med Biol*, 54: N355-365. (2009)

18. H. Liu., G. Ren., Z. Miao, X., Zhang, X., Tang, P. H., S. S. Gambhir, and Z. Cheng, "Molecular optical imaging with radioactive probes," *PLoS ONE* 5:9470, 2010.

19. Li C., Mitchell G., Chemy S. R., "Cerenkov luminescence tomography for small animal imaging" *Optics Letters*, 35: 1109-1111. 2010.

20. Antonello E, S., Chaincy K., Brad W. R., Riccardo C., Pasquina M., Andrea S., and Federico B., "Multispectral Cerenkov luminescence tomography for small animal optical imaging," *Opt. Express* 19:12605-12618, 2011, 21. H. Liu, C. M. Carpenter, H. Jiang, G. Pratx, C. Sun, M. P. Buchin, S. S. Gambhir, L. Xing, Z. Cheng., "Intraoperative imaging of tumors using Cerenkov luminescence endoscopy: A feasibility experimental study", *J. of Nucl. Medicine.*, 2012 (In press).

22. Kosuda S., Kison P. V., et al., "Preliminary assessment of fluorine-18 fluorodeoxyglucose positron emission tomography in patients with bladder cancer", *Euro. J. of Nucl. Med. and Mol. Imag.*, 24: 615-620, 1997.

23. Fibers get special Nature Photonics 5, 461 (2011).

Example 4

Semiconductor nanocrystals, Quantum dots (QDs), exhibit many favorable characteristics including size-dependent tunable emission bands, broad excitation spectra, large molar extinction coefficient, high fluorescence quantum yields, large effective Stokes shifts, and high photostability[1]. Recently, QDs have drawn much attention for their potential biomedical applications and have been widely explored as effective fluorescent sensors for real-time detection of biomolecules, for staining of biological tissues and for molecular imaging of biological pathways or disease progression in vitro and in vivo[2]. However, like many other fluorescence probes, external light is required to illuminate the QDs to produce a fluorescent signal. This limits the in vivo use of QDs due to strong background autofluorescence, poor tissue penetration of the excitation photons, as well as significant absorption and scattering of these photons in tissues. To circumvent these problems, self-illuminating QD conjugates that can emit red to near infrared (NIR) light without external excitation would be ideal. Several promising QD conjugates with such novel characteristics have been described by mimicking a natural bioluminescence resonance energy transfer (BRET) process, in which chemical energy is converted into photons to excite the QDs[3]. This interesting work has inspired us to further develop other direct and specific self-illuminating QD systems with a broad excitation spectrum.

Many radionuclides ($^{18}$F, $^{131/123}$I, $^{99m}$Tc, $^{90}$Y, etc.) have been widely used in the nuclear medicine for diagnostic or therapeutic purpose. Besides emitting high energy particles or γ rays (keV to MeV), radionuclides such as beta emitters ($\beta^+$ and $\beta^-$) have been found to be able to generate low energy lights with continuous wavelengths which are originated from Bremsstrahlung or Cerenkov radiation[4]. In this example it is hypothesized that the radioactive luminescent light at visible and NIR window (1.2-3.1 eV, 400-1000 nm) could serve as an internal source for illumination of many different fluorophores such as QDs, and the resulting fluorescent emissions can then be used for optical imaging (FIG. 4.1). To prove this concept, three CdSe/ZnS core-shell QDs (QD655, QD705 and QD800) were selected and irradiated by a $\beta^-$ emitter, $^{131}$I, for in vitro and in vivo optical imaging.

An IVIS Spectrum system was used to measure the $^{131}$I radiation luminescence intensities at different wavelengths (490 to 850 nm). High light intensity was observed at 490-550 nm. It was slowly reduced at 550-710 nm and then a plateau achieved at 710-850 nm. This continuous emission spectrum overlapped with the absorption spectra of QDs, suggesting the continuous wavelengths of radiation luminescence could be useful for exciting the QD nanocrystals (FIG. 4.2A). Encouraged by this result, we then mixed 0.37 MBq (10 µCi) of Na$^{131}$I with different QDs (QD655, QD705, and QD800, 8 pmol in 300 pt of PBS each) and measured their optical intensities at different wavelengths. Three distinct fluorescence emission peaks at 650, 705 and 800 nm were detected for these three QDs, respectively, while $^{131}$I alone showed much lower optical intensities (FIG. 4.2B). In comparison, the typical fluorescence emission spectra of these QDs were obtained by applying UV light illumination at 465 nm (FIG. 4.2C). Next, the QDs/Na$^{131}$I mixtures were incubated with mouse serum for 60 min and their fluorescence emission properties were determined. These samples displayed similar emission pattern as the QDs/Na$^{131}$I prior to the incubation (FIG. 4.1D). Stronger emission intensity of QD655, compared with QD 705 and QD800, indicated higher illuminating photon absorption of QD655 under our experimental settings (FIGS. 4.2B, 4.C and 4.2D). Therefore QD655 was first chosen for the radioactive luminescence imaging in vivo. Overall, the spectral study demonstrates that radiation luminescent could be used to excite QDs to produce detectable fluorescent lights for optical imaging purpose, and the QDs preserve their fluorescence emission properties under the mouse serum incubation as well as high energy radioactive irradiation for the time frame investigated in this study.

The radioactive luminescence imaging was then performed on IVIS 200 system to test whether the radiation excited QDs can be detected noninvasvely in vivo. Na$^{131}$I (0.37 MBq) alone or QD655/Na$^{131}$I (0.37 MBq) mixture were injected into the murine foreleg or flank either subcutaneously or intramuscularly (see FIG. 4.3A for the injection map), and luminescence imaging (without external light for illumination) was then performed. With the open filter which collects lights from 490 to 850 nm, it was found that Na$^{131}$I did show good optical signals for both injection sites subcutenously (site 1) and intramuscularly (site 3). While site 3 exhibited lower signals than that of the 1, because of its deeper location. More importantly, QD655/Na$^{131}$I (injection sites 2 and 4) exhibited much higher optical intensities than the corresponding Na$^{131}$I, because its luminesecnce signal was contributed by both lumniescence induced by Na$^{131}$I radiation and fluorescence light emitted from QD655 excited by the radiation (FIG. 4.3A). When the filter (575-650 nm) was used, the QD655/Na$^{131}$I showed prominent optical signals, while Na$^{131}$I generated much lower lights (FIG. 4.3B). The fluorescent signal from QD655 alone could be obtained by subtracting the Na$^{131}$I component. Finally, the fluorescent imaging was also performed for the same mice. Under the external UV light excitation (500-550 nm), high optical signals were observed for the injection sites containing QD655, while the locations injected with Na$^{131}$I produced negligibile optical signals (FIG. 4.3C). This study clearly demonstrates that QDs can be detected in vivo using internal radioactivity illumination. More importantly, irradiation can supply the consecutive excitation with a full wavelength range (e.g., From 490 to 850 nm) without changing the excitation filter installation. The sensitivity of this approach could be further improved by a) using different radionuclides which can produce more photons and b) by optimizing imaging instruments and protocols.

Next we then demonstrated the feasibility of using radiation luminescent excited QDs for multiplexing imaging using the IVIS spectrum system. Samples for three types of QDs and their combinations were prepared (QD655, QD705, QD800, QD655+QD705, QD655+QD800, QD705+QD800, QD655+QD705+QD800, and a blank PBS). When the optical lights were collected for QD655 (620-700 nm), samples containing QD655 were lighted up (FIG. 4.4A). When the 660-800 nm lights for QD705 nm was used, all the samples containing QD705 were observed (FIG. 4.4B). The samples containing QD800 were lighted up using the 760-840 nm filter (FIG. 4.4C). Lastly, these eight distinctive samples could be easily differentiated and represented by different colors in the spectra unmixed images (FIG. 4.4D).

Finally, the in vivo multiplexed optical imaging study was performed. Four samples (1: QD655/Na$^{131}$I; 2: QD705/Na$^{131}$I; 3: QD800/Na$^{131}$I; 4: QD655/QD705/QD800/Na$^{131}$I, for all samples, radioactivity is 0.37 MBq) were injected intramuscularly to different locations of the mice (FIG. 4.5A). Similarly, as the in vitro study, when the optical lights were collected for QD655 window (620-700 nm), injection sites 1 and 4 containing QD655 could be clearly imaged with high intensities. Some signals from 2 and 3 were also observed (FIG. 4.5A) due to the Na$^{131}$I radiation luminesecnce and the broad emission spectrum of QD655 (FIGS. 4.2B, 4.2C, 4.2D). When the imaging window (660-800 nm) for QD705 was used, injection sites 2 and 4 containing QD705 were delineated from the surrounding tissues. Very low signals were observed from injection sites 1 and 3 (FIG. 4.5B). Upon using the QD800 imaging window (760-840 nm), injection sites 3 and 4 were seen due to QD800 presenting in the mixture (FIG. 4.5C). Site 2 was also visible because of the spectral overlap of QD705 with QD800. (FIG. 4.2). In vivo QD emission at site 4 (FIGS. 4.5A, 4.5B, 4.5C) showed the same consistent intensity patterns as in vitro (FIG. 4.2B). Radioactive luminescence photons from Na$^{131}$I were taken up by the QDs proportional to their absorption efficiencies; resulting in the observed emission patterns. Lastly, the spectral unmixed image of the same mouse revealed different QDs locations and presence which were represented by different colors (FIG. 4.5D).

In conclusion, this work demonstrates the feasibility of using radiation luminescence as an internal source to illuminate the QDs. Whereas the number of luminescent photons resulted from radionuclides radiation is smaller than that generally produced by other techniques (e.g. BRET, laser illumination), the QDs excited can still produce detectable fluorescence lights both in vitro and in living small animals. Furthermore, multiplexed radioactivity illuminated QDs optical imaging can be achieved in living mice. This study provides an alternate method to excite QDs using internal excitation of broad continuous wavelengths. This is accomplished without applying external excitation, which overcomes some of the barriers current QDs based optical imaging technologies. Compared to the bioluminescent QD based on BRET[3], radioactivity illuminated QD system shows broad excitation spectrum and does not require the stable enzymatic mutants or complex protein engineering. Although radiation illumination could be limited to the half life of the radionuclides, the use of radioactivity provides accessibilities for other imaging modalities (PET, SPECT) in addition to optical imaging. Recently, dual-labeled probes are under active investigations in the molecular probe research field. Radiolabeled QDs bioconjugates have been used for PET ($^{64}$Cu, etc., radioactive component) and optical (QD, fluorescent component) dual modality imaging[5]. Our study indicates this kind of dual-labeled probe could be useful for nuclear imaging and radioactive optical imaging through self-illumination. Overall this study opens new opportunities for using radioactive QDs for in vivo imaging.

EXPERIMENTAL SECTION

Materials: Na$^{131}$I was purchased from Perkin Elmer (Waltham, Mass.). QDs were obtained from Invitrogen Life Technologies (Carlsbad, Calif.). Female athymic nude mice (nu/nu), obtained from Charles River Laboratories, Inc. (Cambridge, Mass.) were at 4-6 weeks of age. A CRC-15R PET dose calibrator (Capintec Inc., Ramsey, N.J.) was used for all radioactivity measurements.

Radioactive optical imaging: In vivo radioactive OI was performed with IVIS 200 and Spectrum systems. Wavelength-resolved spectral imaging was carried out using an 18-set narrow bands emission filters set (490-850 nm). Animals were placed in a light-tight chamber under isofluorane anesthesia. Each acquisition, with or without filters, took 1-3 min for all studies. Images were acquired and analyzed using Living Image 3.0 software (Caliper life sciences, Hopkinton, Mass.). Optical signal was normalized to photons per second per centimeter square per steradian (p/s/cm$^2$/sr). Identical setting was used for in vitro Radioactive OI. For in vivo imaging study, 0.37 MBq (10 µCi) Na$^{131}$I with or without QD(s) were dissolved in 25 µl of PBS, and then mixed with an equal volume of Matrigel (BD Biosciences, Bedford, Mass.) at 4° C. A total volume of 50 µl of Matrigel mixture was injected to normal mice (n=3) subcutaneously or intramuscularly.

References, each of which is Incorporated herein by Reference

[1] a) W. C. Chan, S. Nie, Science 1998, 281, 2016; b) X. Wu, H. Liu, J. Liu, K. N. Haley, J. A. Treadway, J. P. Larson, N. Ge, F. Peale, M. P. Bruchez, *Nat Biotechnol* 2003, 21, 41.

[2] a) I. L. Medintz, H. T. Uyeda, E. R. Goldman, H. Mattoussi, *Nat Mater* 2005, 4, 435; b) X. Michalet, F. F. Pinaud, L. A. Bentolila, J. M. Tsay, S. Doose, J. J. Li, G. Sundaresan, A. M. Wu, S. S. Gambhir, S. Weiss, Science 2005, 307, 538.

[3] a) M. K. So, C. Xu, A. M. Loening, S. S. Gambhir, J. Rao, *Nat Biotechnol* 2006, 24, 339; b) H. Yao, Y. Zhang, F. Xiao, Z. Xia, J. Rao, *Angew Chem Int Ed Engl* 2007, 46, 4346; c) Y. Xing, J. Rao, *Cancer Biomark* 2008, 4, 307.

[4] a) P. A. Cerenkov, Physical Review 1937, 52, 0378; b) H. H. Ross, *Analytical Chemistry* 1969, 41, 1260; c) S. M. Seltzer, M. J. Berger, *Nuclear Instruments & Methods in Physics Research Section B-Beam Interactions with Materials and Atoms* 1985, 12, 95; d) W. Nakel, *Physics Reports-Review Section of Physics Letters* 1994, 243, 317.

[5] a) M. L. Schipper, Z. Cheng, S. W. Lee, L. A. Bentolila, G. Iyer, J. Rao, X. Chen, A. M. Wu, S. Weiss, S. S. Gambhir, *J Nucl Med* 2007, 48, 1511; b) W. Cai, K. Chen, Z. B. Li, S. S. Gambhir, X. Chen, *J Nucl Med* 2007, 48, 1862.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to what is being measured. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim at least the following:

1. A method of imaging a target within a living subject or a sample comprising:
   introducing one or more radionuclide probes into the living subject or sample; and
   detecting low energy photons from one or more radionuclide probes as optical signals, wherein the low energy photon have an energy of less than 0.005 keV.

2. The method of claim 1, wherein one or more of the radionuclide probes have an affinity for a target in the living subject or the sample.

3. The method of claim 2, further comprising:
   processing data corresponding to the detected optical signals to provide an image of the target.

4. The method of claim 2, further comprising:
   processing data corresponding to the detected optical signals to provide a 3-dimensional image of the target.

5. The method of claim 2, further comprising:
   processing data corresponding to the detected optical signals to provide a planar image of the target.

6. The method of claim 1, wherein the optical signals have a wavelength in the visible or infrared or a combination thereof.

7. The method of claim 2, further comprising: identifying an area from which the optical signal is produced, wherein area corresponds to the target.

8. The method of claim 1, wherein the target is a cellular abnormality that is indicative of a disease.

9. The method of claim 8, further comprising: evaluating the status of the disease by comparing the image with a previous image.

10. The method of claim 8, further comprising: monitoring the regression of the disease.

11. The method of claim 1, further comprising: determining pharmacokinetic parameters of an experimental or pharmacological molecule in the living subject or the sample.

12. The method of claim 2, further comprising: real-time monitoring of surgery at a surgical region of interest, optionally, wherein the region of interest includes the target.

13. The method of claim 1, wherein the disease is selected from the group consisting of: cancer, inflammatory disease, immunological disease, neurodegenerative disease, cardiovascular disease, and an infectious disease.

14. The method of claim 13, wherein cancer is selected from the group consisting of: breast cancer, ovarian cancer, cervical cancer, pancreas cancer, colorectal cancer, prostate cancer, lung cancer, brain tumor, skin cancer, gastrointestinal cancer, esophageal cancer, mouth cancer, bone cancer, and renal cancer.

15. The method of claim 1, wherein the sample is a tissue selected from the group consisting of: colon, lung, bronchi, breast, thyroid, pancreas, kidneys, ovaries, cervix, prostate, brain, skin, gastrointestinal tract, esophagus, mouth, and bone tissue.

16. The method of claim 1, wherein the radionuclide include radionuclides except those that are pure gamma rays-emitting radionuclides.

17. The method of claim 1, wherein the radionuclide is selected from the group consisting of: $^{11}$C, $^{13}$N, $^{15}$O $^{18}$F, $^{68}$Ga $^{131}$I, $^{90}$Y, $^{177}$Lu, $^{123}$I, $^{111}$In, $^{211}$At, $^{212}$Bi, $^{213}$Bi, $^{223}$Ra, $^{225}$Ac, $^{67}$Cu, $^{111}$Ag, $^{131}$I, $^{149}$Pm, $^{153}$Sm, $^{166}$Ho, $^{177}$Lu, $^{186}$Re, $^{188}$Re, $^{211}$At, $^{212}$Bi, $^{213}$Bi, and $^{223}$Ra.

18. A system for imaging a target within a living subject or a sample, comprising:
   an optical detection system configured to detect low energy photons from one or more radionuclides as optical signals within said living subject or sample, wherein the low energy photon have an energy of less than 0.005 keV; and
   an optical signal processing system configured to provide images based upon the optical signal;
   wherein the optical detection system comprises photonic devices to detect and to transmit low energy photons generated by one or more radionuclide as optical signals.

19. A method for analyzing an optical signal emitted by one or more radionuclides, comprising:
   detecting low energy photons from one or more radionuclides as optical signals, wherein the low energy photon have an energy of less than 0.005 keV; and
   processing data corresponding to the detected optical signals to provide information about the optical signal emitted by the one or more radionuclides.

20. The method of claim 19, wherein the information corresponds to an amount of optical signal emitted by one or more radionuclides.

21. The method of claim 19, wherein the information corresponds to the identification of the one or more radionuclide.

22. The method of claim 19, wherein the radionuclide include radionuclides except those that are pure gamma rays-emitting radionuclides.

23. The method of claim 19, wherein the radionuclide is selected from the group consisting of: $^{11}$C, $^{13}$N, $^{15}$O, $^{18}$F, $^{68}$Ga, $^{131}$I, $^{90}$Y, $^{177}$Lu, $^{123}$I, $^{111}$In, $^{211}$At, $^{212}$Bi, $^{213}$Bi, $^{223}$Ra, $^{225}$Ac, $^{67}$Cu, $^{111}$Ag, $^{131}$I, $^{149}$Pm, $^{153}$Sm, $^{166}$Ho, $^{177}$Lu, $^{186}$Re, $^{188}$Re, $^{211}$At, $^{212}$Bi, $^{213}$Bi, and $^{223}$Ra.

* * * * *